United States Patent
Miller-Lionberg et al.

(10) Patent No.: US 10,488,305 B2
(45) Date of Patent: Nov. 26, 2019

(54) PORTABLE AIR SAMPLING DEVICE

(71) Applicant: Colorado State University Research Foundation, Fort Collins, CO (US)

(72) Inventors: Daniel D. Miller-Lionberg, Denver, CO (US); Casey William Quinn, Olympia, WA (US); John Volckens, Fort Collins, CO (US); David Leith, Chapel Hill, NC (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 15/442,657

(22) Filed: Feb. 25, 2017

(65) Prior Publication Data
US 2017/0370809 A1    Dec. 28, 2017

Related U.S. Application Data

(60) Provisional application No. 62/354,019, filed on Jun. 23, 2016.

(51) Int. Cl.
| | |
|---|---|
| *G01N 1/22* | (2006.01) |
| *G01N 15/02* | (2006.01) |
| *G01N 15/06* | (2006.01) |
| *G01N 15/00* | (2006.01) |

(52) U.S. Cl.
CPC .......... *G01N 1/2273* (2013.01); *G01N 1/2202* (2013.01); *G01N 15/0255* (2013.01); *G01N 15/0618* (2013.01); *G01N 2015/0046* (2013.01); *G01N 2015/0693* (2013.01)

(58) Field of Classification Search
CPC .......... G01N 2001/2223; G01N 1/2211; G01N 1/2202; G01N 2001/2276
USPC .............................................. 73/28.01, 28.04
See application file for complete search history.

(56) References Cited

U.S. PATENT DOCUMENTS

| | | | | | |
|---|---|---|---|---|---|
| 4,178,794 A | * | 12/1979 | Jugle | ................ | G01N 1/2202 55/467 |
| 4,183,247 A | * | 1/1980 | Allen | ................ | G01N 1/2273 600/532 |
| 4,432,248 A | * | 2/1984 | Lalin | ................ | G01N 1/2273 73/863.03 |
| 4,796,475 A | * | 1/1989 | Marple | ............. | G01N 1/2205 422/70 |
| 4,827,779 A | * | 5/1989 | Marple | ............. | G01N 1/2205 73/863.22 |
| 4,941,899 A | * | 7/1990 | Liu | .................. | G01N 1/2211 55/337 |

(Continued)

OTHER PUBLICATIONS

Miller, Arthur, et al. "A handheld electrostatic precipitator for sampling airborne particles and nanoparticles." Aerosol Science and Technology 44.6 (2010): 417-427.*

(Continued)

*Primary Examiner* — Daniel S Larkin
(74) *Attorney, Agent, or Firm* — Faegre Baker Daniels LLP

(57) ABSTRACT

A sampling device is constructed having an airflow path from a size-selective inlet to a device outlet, without using any tubing. The size-selective inlet includes at least one of an impactor, a filter, a cyclone, and an inhalable inlet. The device includes a sampling assembly configured to be removably coupled directly to a sampling device housing (e.g., without using tubing), and an airflow assembly that may be constructed without using tubing.

18 Claims, 18 Drawing Sheets

(56) References Cited

U.S. PATENT DOCUMENTS

| | | | | | |
|---|---|---|---|---|---|
| 4,961,916 | A | * | 10/1990 | Lesage | B01D 53/30 422/109 |
| 5,018,395 | A | * | 5/1991 | Hickox | F04D 17/16 73/23.2 |
| 5,333,511 | A | * | 8/1994 | Boyum | G01N 1/2273 323/299 |
| 5,412,975 | A | * | 5/1995 | Raabe | B01D 45/04 73/28.04 |
| 5,702,506 | A | * | 12/1997 | Shih | B01D 46/12 55/343 |
| 6,014,888 | A | * | 1/2000 | Noritake | B01D 53/0407 73/23.35 |
| 7,651,543 | B1 | * | 1/2010 | Marple | G01N 1/2205 55/315 |
| 8,205,511 | B1 | * | 6/2012 | Chen | G01N 1/2211 73/863.21 |
| 8,243,274 | B2 | * | 8/2012 | Aiken | G01M 15/108 356/438 |
| 8,459,098 | B2 | * | 6/2013 | Lee | G01N 1/2211 73/23.3 |
| 8,689,648 | B1 | * | 4/2014 | Heff | G01N 1/2273 73/863.22 |
| 8,973,447 | B2 | * | 3/2015 | Volckens | 73/863.12 |
| 9,506,843 | B2 | * | 11/2016 | Peters | G01N 1/2208 |
| 2003/0008341 | A1 | * | 1/2003 | Spurrell | G01N 1/2205 435/34 |
| 2005/0092065 | A1 | * | 5/2005 | Tajima | G01N 1/2205 73/23.2 |
| 2011/0277679 | A1 | * | 11/2011 | Good | G01N 1/2202 116/202 |
| 2013/0276517 | A1 | * | 10/2013 | Takano | G01M 3/16 73/40.5 R |
| 2016/0153884 | A1 | * | 6/2016 | Han | G01N 1/2205 73/1.06 |
| 2017/0023458 | A1 | * | 1/2017 | Hart | G01N 21/53 |

OTHER PUBLICATIONS

Gerlach, Torsten, and Helmut Wurmus. "Working principle and performance of the dynamic micropump." Sensors and Actuators A: Physical 50.1-2 (1995): 135-140.*

Kenny, L. C., and R. A. Gussman. "Characterization and modelling of a family of cyclone aerosol preseparators." Journal of Aerosol Science 28.4 (1997): 677-688.*

Kenny, L. C., and R. A. Gussman. "A direct approach to the design of cyclones for aerosol-monitoring applications." Journal of aerosol science31.12 (2000): 1407-1420.*

Hsiao, Ta-Chih, Da-Ren Chen, and Sang Young Son. "Development of mini-cyclones as the size-selective inlet of miniature particle detectors." Journal of Aerosol Science 40.6 (2009): 481-491.*

Chakrabarti, Bhabesh, et al. "Performance evaluation of the active-flow personal DataRAM PM 2.5 mass monitor (Thermo Anderson pDR-1200) designed for continuous personal exposure measurements." Atmospheric Environment 38.20 (2004): 3329-3340.*

PDR-1000AN & PDR-1200S Instruction Manual. Thermo Electron Corporation. (2004): 1-54.*

Cate, David M., et al. "Rapid detection of transition metals in welding fumes using paper-based analytical devices." Annals of occupational hygiene 58.4 (2014): 413-423.*

Ramanathan, N., et al. "A cellphone based system for large-scale monitoring of black carbon." Atmospheric environment 45.26 (2011): 4481-4487.*

Applicant: Colorado State University Research Foundation. "Notification of Transmittal of the International Search Report and the Written Opinion of the International Searching Authority, or the Declaration". International Application No. PCT/US2017/038847. 18 pages. International Filing Date: Jun. 22, 2017. dated Nov. 2, 2017.

International Preliminary Report on Patentability issued in PCT/US2017/038847, dated Jan. 3, 2019, 10 pages.

The International Search Report and Written Opinion issued in PCT/US2017/038847, dated Nov. 2, 2017, 18 pages.

* cited by examiner

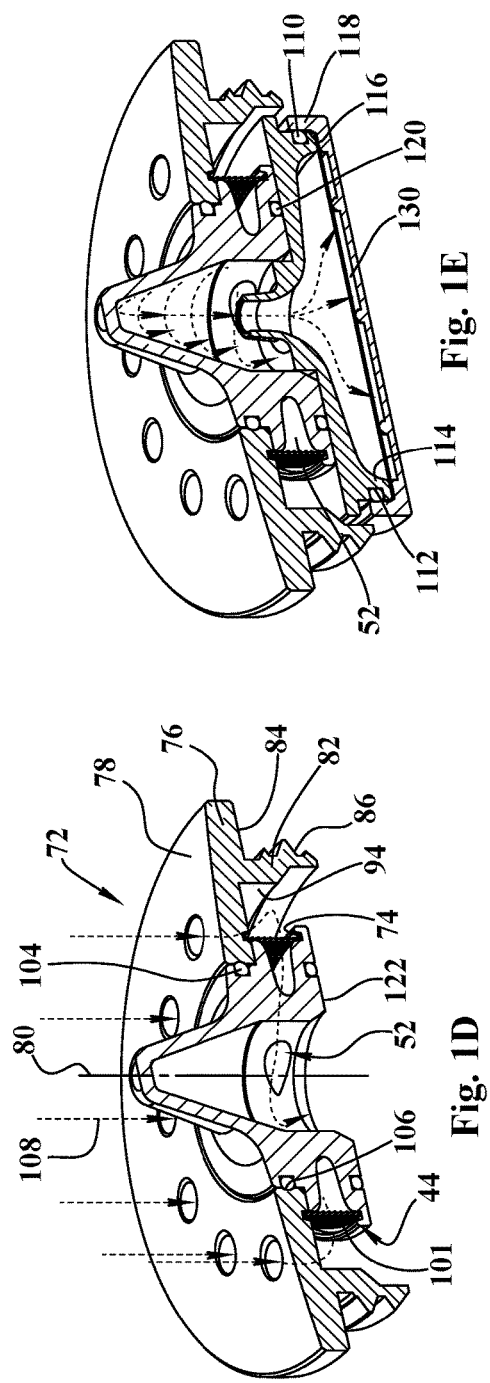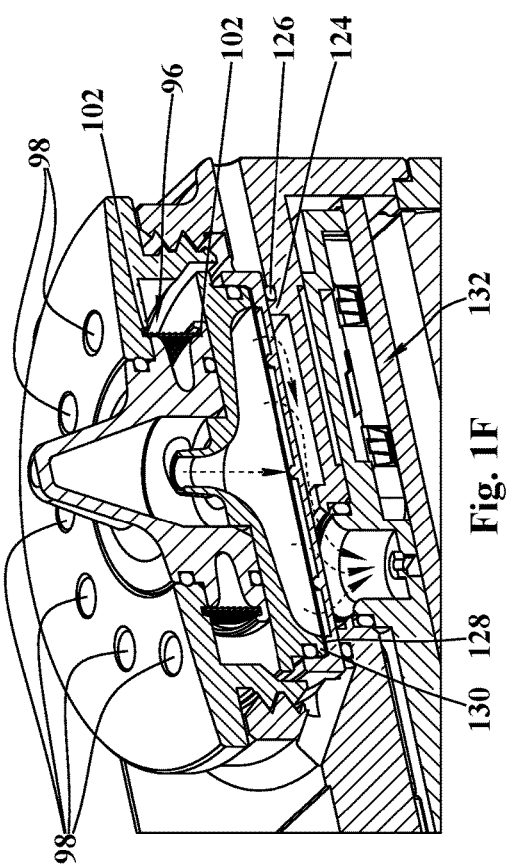

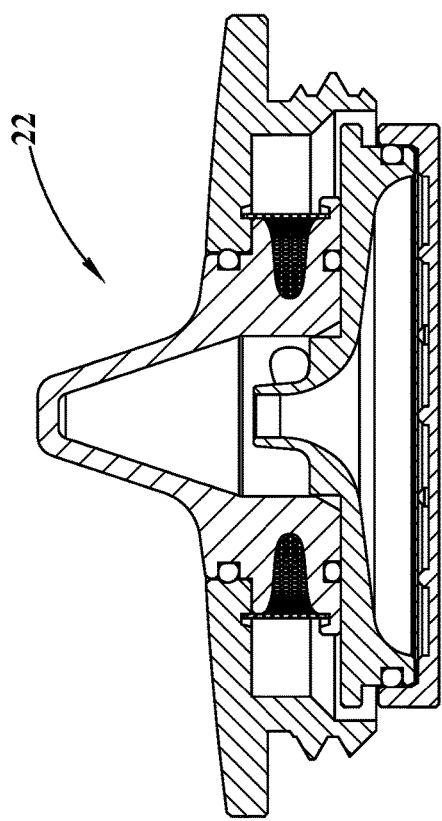
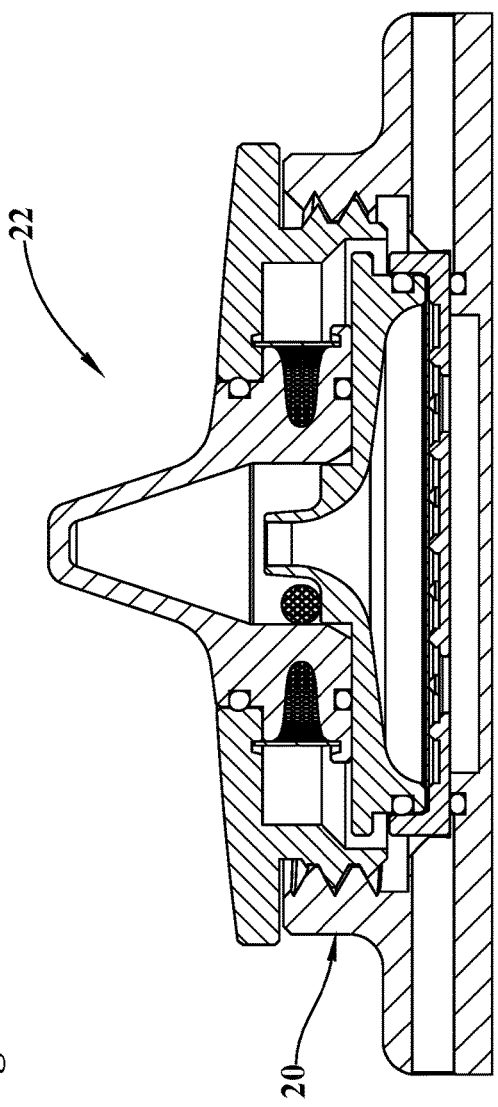
Fig. 1G
Fig. 1H

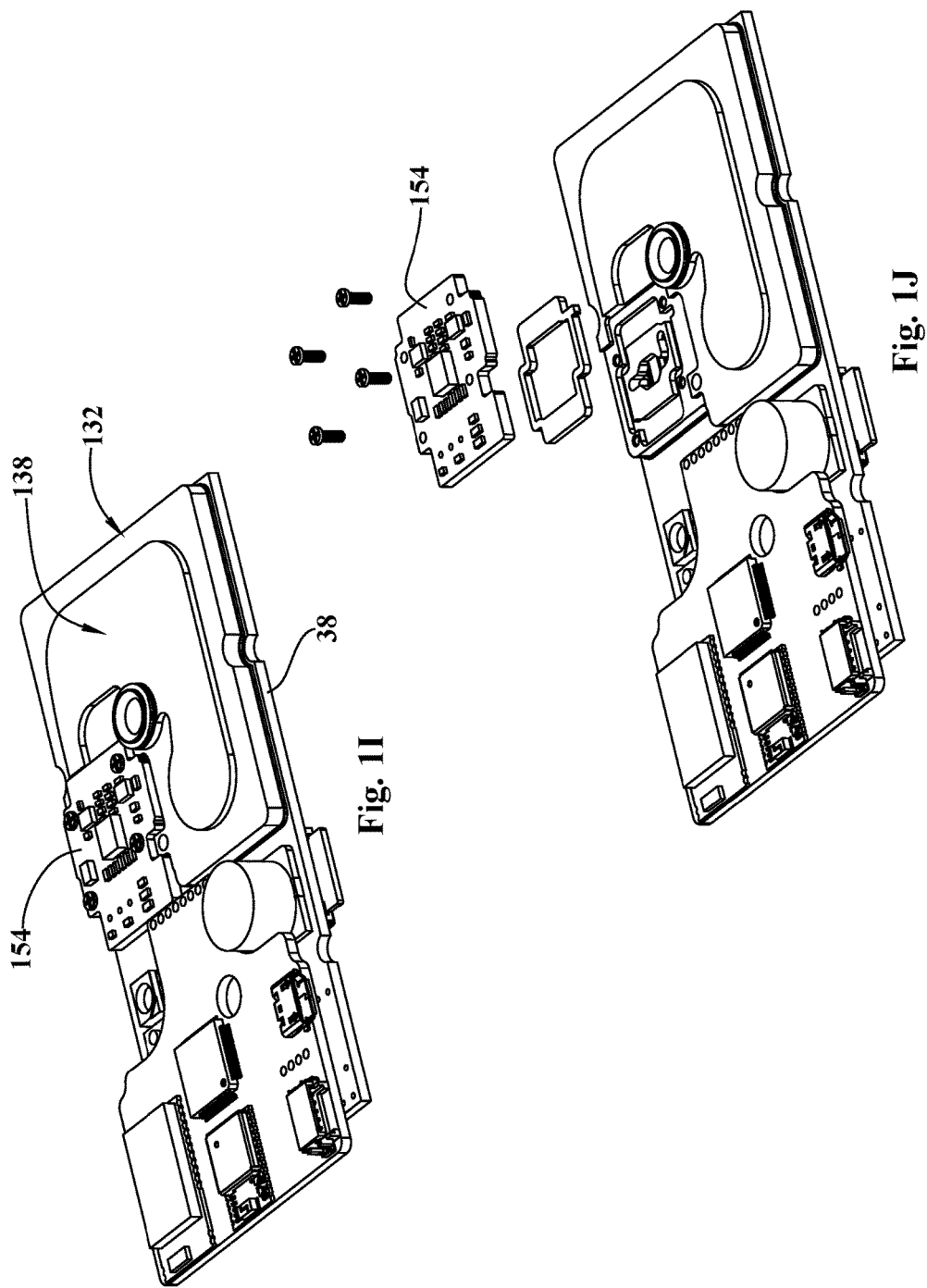

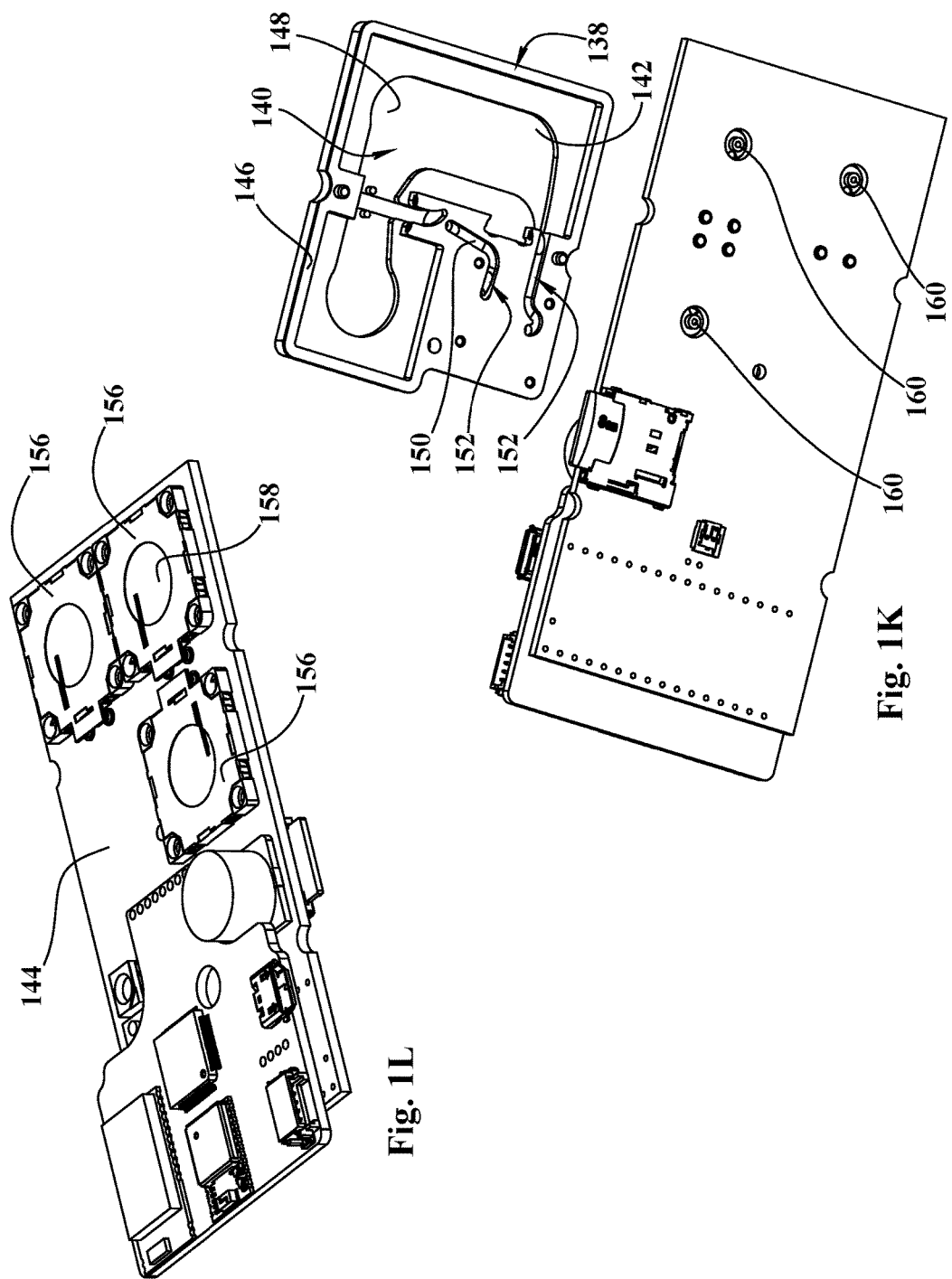

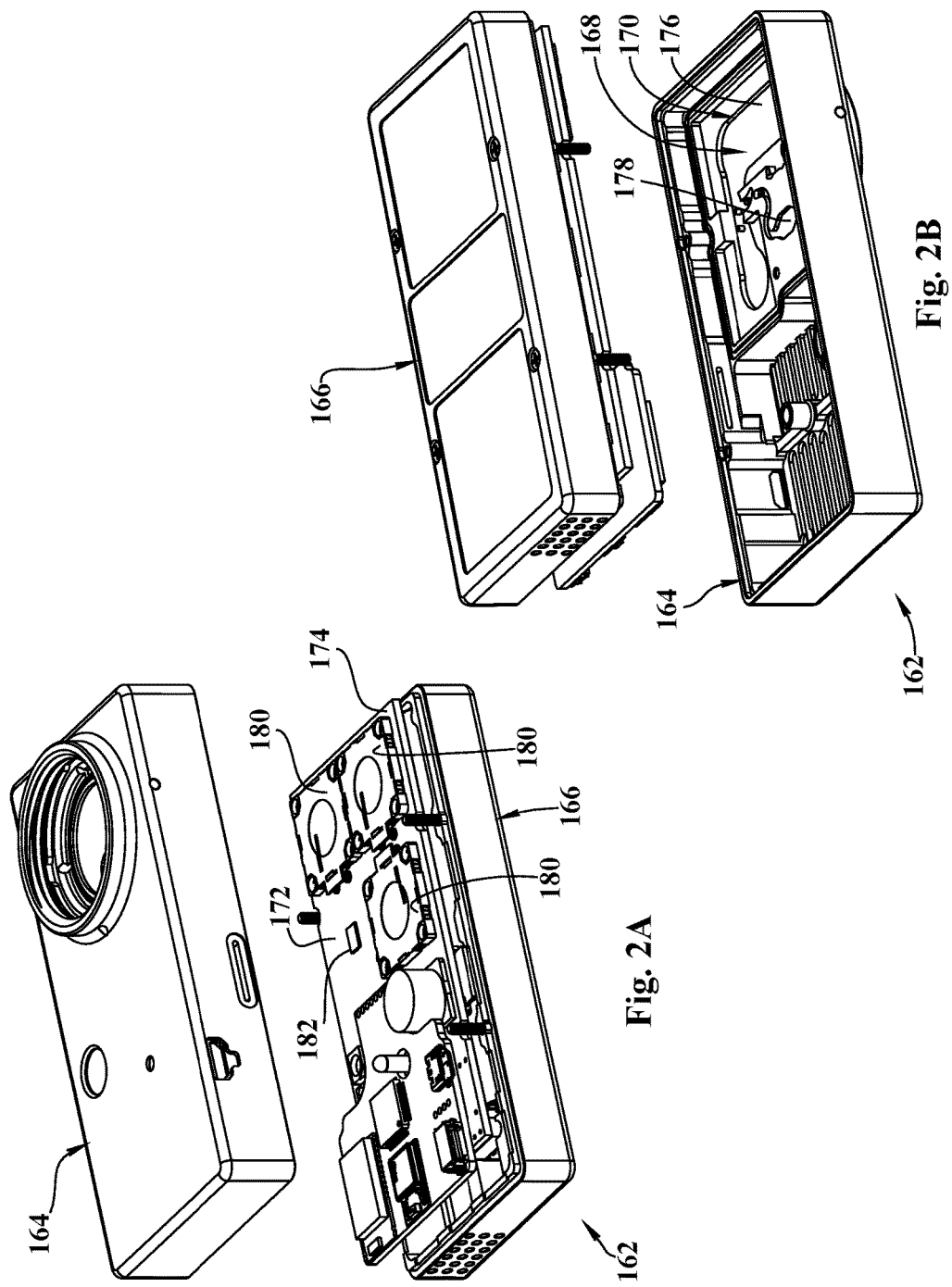

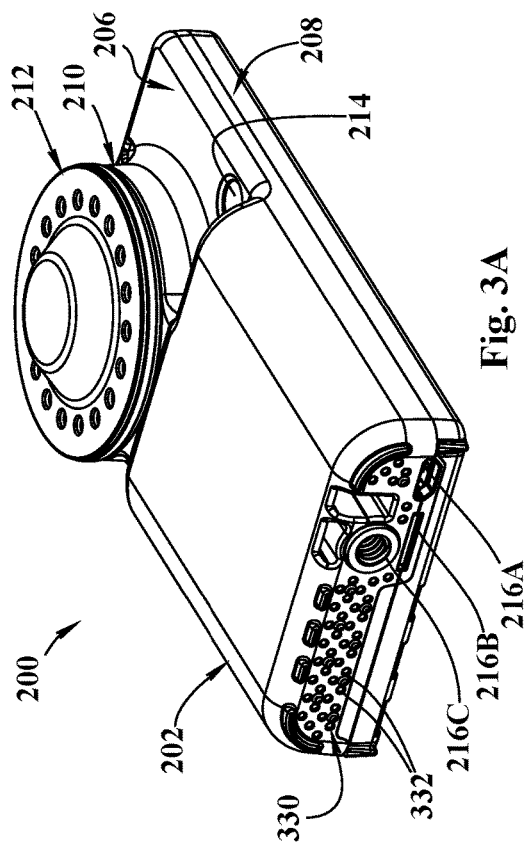
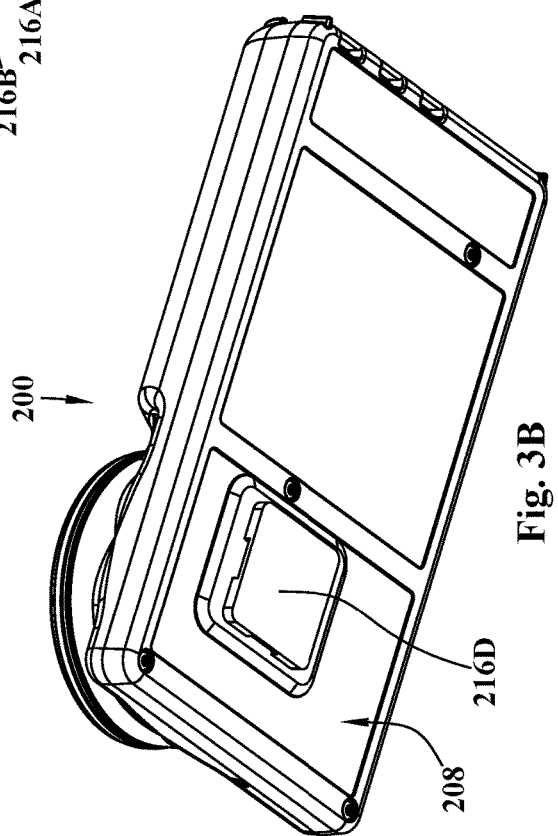
Fig. 3A
Fig. 3B

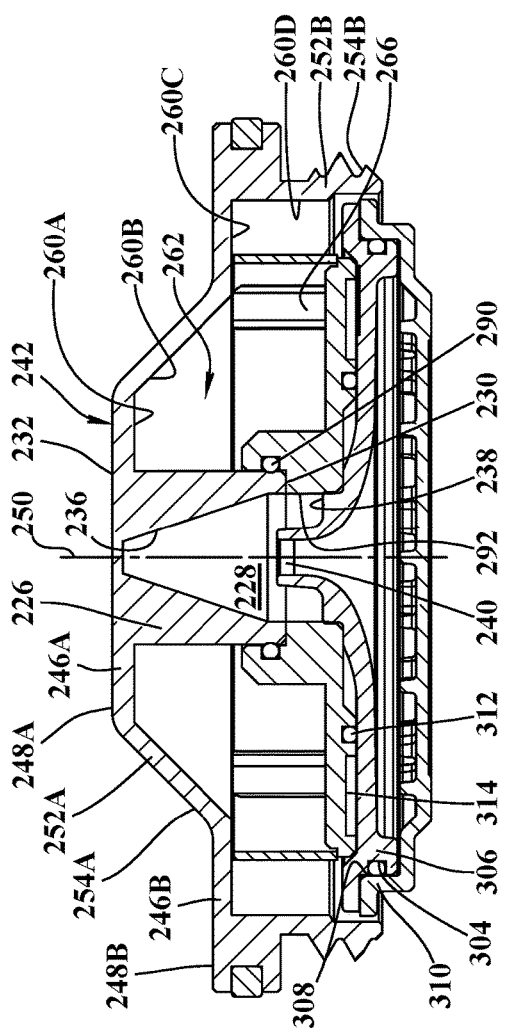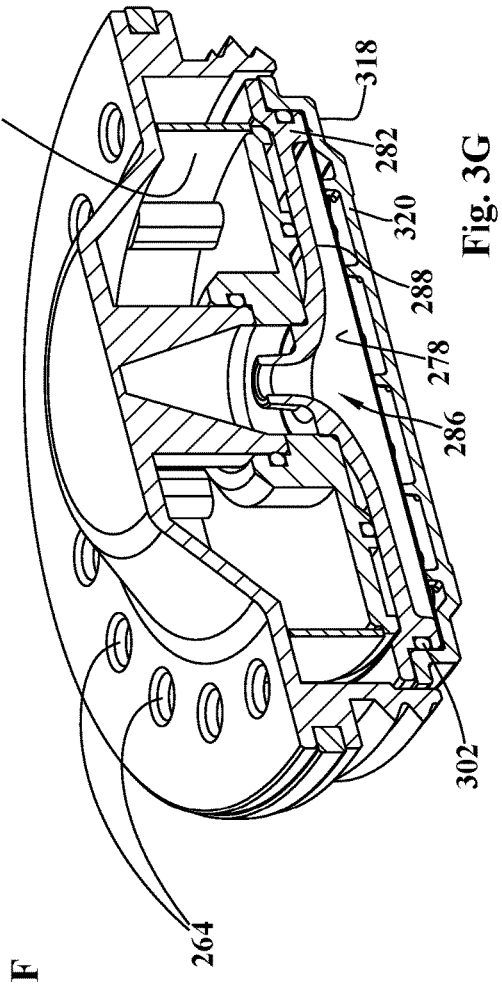
Fig. 3F
Fig. 3G

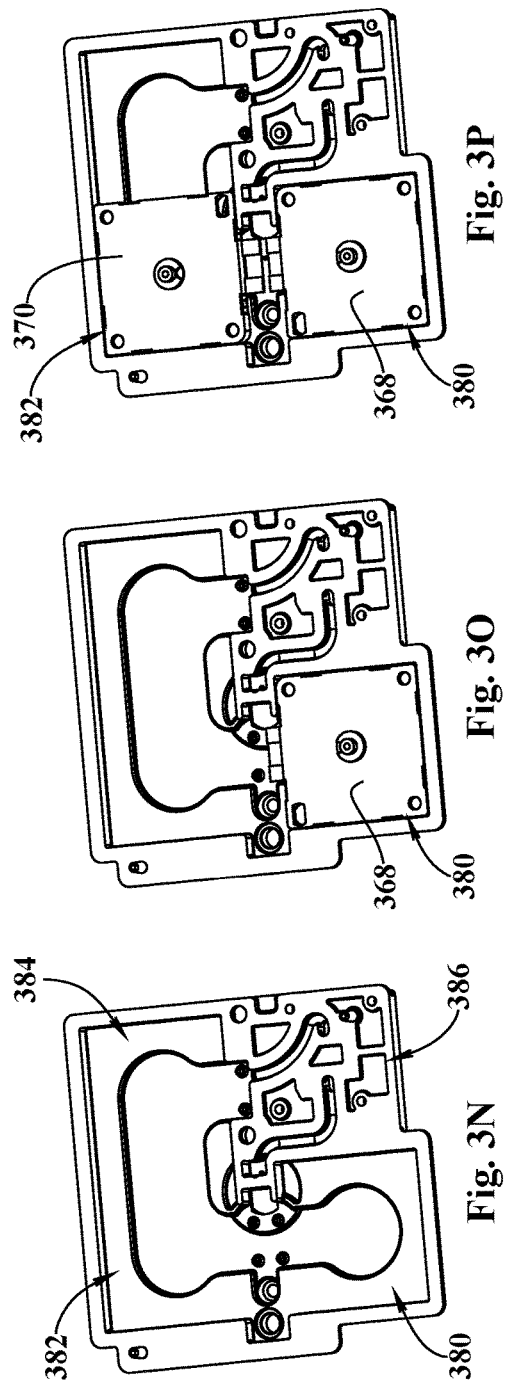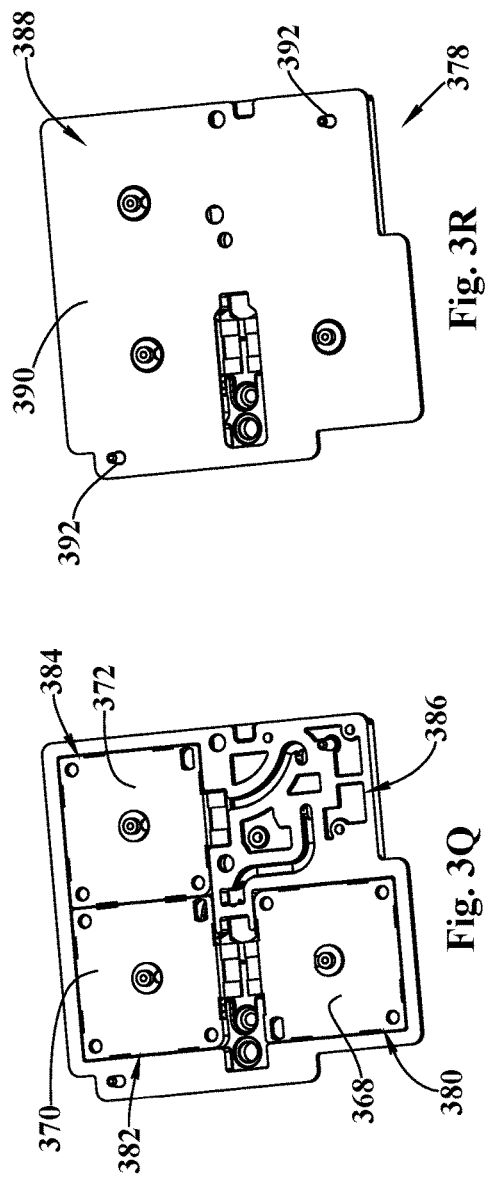

PORTABLE AIR SAMPLING DEVICE

CROSS-REFERENCE TO RELATED APPLICATIONS

This application claims priority to U.S. Provisional Application No. 62/354,019, filed Jun. 23, 2016, entitled "Development and Evaluation of an Ultrasonic Personal Aerosol Sampler (UPAS)," which is hereby incorporated by reference in its entirety for all purposes.

STATEMENT REGARDING FEDERALLY SPONSORED RESEARCH OR DEVELOPMENT

This invention was made with government support under grants OH010662 and ES024719 awarded by National Institutes of Health. The government has certain rights in the invention.

FIELD

Embodiments of the disclosed subject matter include portable air sampling devices. More specifically, embodiments of the disclosure are directed to portable, size-selective aerosol sampling devices.

BACKGROUND

Indoor and outdoor air pollution are major global contributors to human disease, disability, and mortality. Household air pollution, which, in developing countries, results primarily from the incomplete combustion of primitive fuels for cooking and heating (e.g., wood, charcoal, etc.), is considered the $6^{th}$ leading risk factor for disease and death on the planet. Outdoor air pollution from particulate matter, which results primarily from the combustion of fossil fuels for power generation and transportation, is considered the $11^{th}$ leading risk factor.

Despite these alarming statistics, current understanding of human exposure to air pollution (whether indoors or outdoors) is limited. Although regulatory agencies such as the U.S. Environmental Protection Agency maintain national air quality monitoring networks, the monitors underlying these networks tend to be relatively sparse, costly to maintain, and report only outdoor pollution levels. Furthermore, data from such monitoring networks only modestly correlate with an individual's daily exposure to air pollution. Since the vast majority of people spend their lives indoors, moving from one microenvironment to the next (e.g., at home, at work, or in transit), assessment of personal exposure remains the standard for determining individual risk. Studies that have examined personal exposure to air pollution, however, have consistently demonstrated lognormal variations in exposure that span both space and time. Characterizing lognormal exposure distributions requires studies with relatively large sample sizes; however, most of these studies are limited to modest sample sizes because of limitations in the technologies used to assess personal exposure.

A major constraint on the current ability to assess personal air pollution exposure is the cost and physical burden of the monitors themselves. For monitoring exposure to particulate matter (PM), personal air samplers typically consist of a battery-powered diaphragm pump connected by tubing to a size-selective inlet (e.g., a cyclone or impactor) to measure inhalable, respirable, or $PM_{2.5}$ size fractions of particulate matter within the wearer's breathing zone. Such personal air samplers are expensive (typically costing >$1500 each), relatively heavy (>0.5 kg in total), and noisy (emitting >60 dB from the pump). The physical burden posed by these monitors (noise, visual aesthetic, and weight) make them difficult to wear for extended periods. Further, the diaphragm pumps must be periodically checked for flow accuracy and the tubing connections often disconnect or become pinched if the wearer is physically active. For these reasons, studies of personal PM exposure often suffer from small sample size and data loss due to poor user compliance and instrument reliability.

Historically, the development of PM exposure monitors was driven by the need to assess occupational intake for aerosol hazards in the dusty trades such as mining, construction, manufacturing, and agriculture. In those workplaces, the weight and noise of the monitors was less of a hindrance. For personal monitoring among the general population (or outside of heavy industry), however, a need exists for technology that overcomes these limitations. Therefore, there is a need for a wearable and portable air pollution monitor to address the numerous limitations of currently available monitors, without sacrificing precision, accuracy, and reliability.

SUMMARY

A sampling device is constructed having an airflow path from a size-selective inlet to a device outlet, without using any tubing. The size-selective inlet includes at least one of an impactor, a filter, a cyclone, and an inhalable inlet. The device includes a sampling assembly configured to be removably coupled directly to a sampling device housing (e.g., without using tubing), and an airflow assembly that may be constructed without using tubing.

In an Example 1, a portable, size-selective aerosol sampling device, comprising: a housing at least partially enclosing an inner chamber, the housing comprising an upper housing portion and a lower housing portion, the upper housing portion comprising a size-selective inlet; and an airflow assembly disposed within the inner chamber and comprising a portion of an airflow path from the size-selective inlet through the sampling device to an airflow outlet of the sampling device, the airflow assembly comprising: a portion of a printed circuit board (PCB); and a manifold configured to be sealably coupled to the portion of the PCB to define at least one airflow channel disposed between an inner surface of the manifold and an outer surface of the PCB.

In an Example 2, the sampling device of Example 1, wherein the manifold comprises a plurality of inside surfaces of the upper housing portion or the lower housing portion.

In an Example 3, the sampling device of Example 1, wherein the manifold comprises a monolithic part created using at least one of an injection-molding process, a three-dimensional printing process, and a machining process.

In an Example 4, the sampling device of any of Examples 1-3, wherein a seal between the manifold and the PCB is achieved using at least one of an adhesive and a compressible gasket.

In an Example 5, the sampling device of any of Examples 1-4, further comprising one or more sensors mounted to the outer surface of the PCB and disposed between the inner surface of the manifold and the outer surface of the PCB.

In an Example 6, the sampling device of any of Examples 1-5, further comprising one or more pumping elements, each having an inlet exposed to a first environment and an outlet exposed to a second environment, wherein each outlet is sealed from the first environment at an interface with at least one of the inner surface of the manifold and the outer surface of the PCB.

In an Example 7, the sampling device of Example 6, the one or more pumping elements comprising one or more ultrasonic micropumps.

In an Example 8, the sampling device of any of Examples 1-7, wherein the at least one airflow channel comprises a primary airflow channel, the manifold comprising: an interface surface configured to mate with an interface portion of the outer surface of the PCB; and at least one inner channel surface defining the primary airflow channel.

In an Example 9, the sampling device of Example 8, the manifold further comprising at least one additional inner surface configured to partially define at least one secondary airflow channel, wherein the at least one secondary airflow channel is configured to provide airflow to an inlet of a mass flow sensor, the mass flow sensor comprising an outlet that opens into an ambient environment having an ambient air pressure, and wherein the mass flow sensor is configured to obtain measurements to facilitate estimation of at least one of a pressure drop across a sampling filter and an aerosol mass accumulation rate onto a sampling filter, the ambient environment comprising at least one of the inner chamber and an environment outside of the housing.

In an Example 10, the sampling device of any of Examples 1-9, wherein the size-selective inlet comprises at least one of an impactor, a filter, a cyclone and an inhalable inlet.

In an Example 11, the sampling device of any of Examples 1-10, further comprising an optical sensor for determining one or more air quality parameters.

In an Example 12, the sampling device of any of Examples 1-10, wherein the airflow path does not include tubing.

In an Example 13, the sampling device of any of Examples 1-12, further comprising a sampling assembly having a coupling interface configured to be removably mated with a corresponding coupling interface of the sampling assembly receiver, the sampling assembly comprising a cyclone assembly, the cyclone assembly comprising: a cyclone body having an at least partially conical cavity defined therein, wherein the cavity extends from a lower end of the cyclone body toward an upper end of the cyclone body; a cyclone inlet aperture defined through the cyclone body; a cyclone floor disposed adjacent the lower end of the cyclone body; and a size-selective cyclone outlet aperture defined through the cyclone floor.

In an Example 14, the sampling device of Example 13, the sampling assembly further comprising a filter cartridge comprising a filter cartridge housing configured to house a sampling filter, the filter cartridge housing comprising: a filter cartridge base configured to receive the sampling filter; and a filter cartridge cap detachably coupled to the filter cartridge base, wherein an upper surface of the filter cartridge cap comprises the cyclone floor.

In an Example 15, the sampling device of either of Examples 13 or 14, wherein characteristics of the size-selective cyclone are configured to allow particulate matter having a selection size to pass through the size-selective cyclone outlet aperture for deposition on a sampling filter, wherein the selection size comprises at least one of an aerodynamic diameter of between approximately 1.0 microns and approximately 10.0 microns, Respirable PM, Thoracic PM, and Inhalable PM.

In an Example 16, the sampling device of any of Examples 1-15, further comprising: a first automatic-identification (AID) component associated with the sampling assembly; and a second AID component associated with the housing, wherein the first and second AID components are configured to communicate using an AID technique, the AID technique comprising at least one of an electronic-contact identification technique, a near-field communication (NFC) technique, and a radio-frequency identification (RFID) technique.

In an Example 17, the sampling device of any of Examples 13-16, the sampling assembly further comprising a sampling assembly skirt disposed around at least a portion of an outside surface of the cyclone body, the sampling assembly skirt comprising: an upper wall having an upper surface that is at least approximately perpendicular to a central vertical axis of the cyclone body; and a side wall extending downward from a lower surface of the upper wall, wherein an outside surface of the side wall is configured to mate with an inner surface of the sampling assembly receiver, wherein the upper surface of the upper wall and an inner surface of the side wall at least partially define a screening chamber into which air is configured to flow before entering the cyclone, and wherein the upper wall includes at least one inlet aperture extending between the upper surface of the upper wall and the lower surface of the upper wall, configured to provide an airflow pathway between an external environment and the screening chamber.

In an Example 18, the sampling device of Example 17, further comprising one or more water-release apertures defined through the sampling assembly receiver and configured to facilitate drainage of water from the screening chamber.

In an Example 19, a portable size-selective aerosol sampling device, comprising: a housing at least partially enclosing an inner chamber, the housing comprising an upper housing portion and a lower housing portion, the upper housing portion comprising a sampling assembly receiver; and a sampling assembly having a coupling interface configured to be removably mated with a corresponding coupling interface of the sampling assembly receiver, the sampling assembly comprising a cyclone assembly, the cyclone assembly comprising: a cyclone body having an at least partially conical cavity defined therein, wherein the cavity extends from a lower end of the cyclone body toward an upper end of the cyclone body; a cyclone inlet aperture defined through the cyclone body; a cyclone floor disposed adjacent the lower end of the cyclone body; a size-selective cyclone outlet aperture defined through the cyclone floor.

In an Example 20, the sampling device of Example 19, the sampling assembly further comprising a filter cartridge comprising a filter cartridge housing configured to house a sampling filter, the filter cartridge housing comprising: a filter cartridge base configured to receive the sampling filter; and a filter cartridge cap detachably coupled to the filter cartridge base, wherein an upper surface of the filter cartridge cap comprises the cyclone floor.

In an Example 21, the sampling device of either of Examples 19 or 20, wherein characteristics of the size-selective cyclone are configured to allow particulate matter having a selection size to pass through the size-selective cyclone outlet aperture for deposition on a sampling filter, wherein the selection size comprises at least one of an aerodynamic diameter of between approximately 1.0 microns and approximately 10.0 microns, Respirable PM, Thoracic PM, and Inhalable PM.

In an Example 22, the sampling device of any of Examples 19-21, further comprising: a first automatic-identification (AID) component associated with the sampling assembly; and a second AID component associated with the housing, wherein the first and second AID components are configured to communicate using an AID technique, the AID technique comprising at least one of an electronic-contact identification technique, a near-field communication (NFC) technique, and a radio-frequency identification (RFID) technique.

In an Example 23, the sampling device of any of Examples 19-22, the sampling assembly further comprising a sampling assembly skirt disposed around at least a portion of an outside surface of the cyclone body, the sampling assembly skirt comprising: an upper wall having an upper surface that is at least approximately perpendicular to a central vertical axis of the cyclone body; and a side wall extending downward from a lower surface of the upper wall, wherein an outside surface of the side wall is configured to mate with an inner surface of the sampling assembly receiver, wherein the upper surface of the upper wall and an inner surface of the side wall at least partially define a screening chamber into which air is configured to flow before entering the cyclone, and wherein the upper wall includes at least one inlet aperture extending between the upper surface of the upper wall and the lower surface of the upper wall, configured to provide an airflow pathway between an external environment and the screening chamber.

In an Example 24, the sampling device of Example 23, further comprising one or more water-release apertures defined through the sampling assembly receiver and configured to facilitate drainage of water from the screening chamber.

In an Example 25, the sampling device of any of Examples 19-24, further comprising an airflow assembly disposed within the inner chamber and comprising a portion of an airflow path from the cyclone inlet aperture through the sampling device to an airflow outlet of the sampling device, wherein the airflow path does not include tubing.

In an Example 26, the sampling device of Example 25, the airflow device comprising: a portion of a printed circuit board (PCB); and a manifold configured to be sealably coupled to the portion of the PCB to define at least one airflow channel disposed between an inner surface of the manifold and an outer surface of the PCB.

In an Example 27, the sampling device of Example 26, wherein the manifold comprises a plurality of inside surfaces of the upper housing portion or the lower housing portion.

In an Example 28, the sampling device of Example 26, wherein the manifold comprises a monolithic part created using at least one of an injection-molding process, a three-dimensional printing process, and a machining process.

In an Example 29, the sampling device of any of Examples 26-28, wherein a seal between the manifold and the PCB is achieved using at least one of an adhesive and a compressible gasket.

In an Example 30, the sampling device of any of Examples 26-29, further comprising one or more sensors mounted to the outer surface of the PCB and disposed between the inner surface of the manifold and the outer surface of the PCB.

In an Example 31, the sampling device of any of Examples 26-30, further comprising one or more pumping elements, each having an inlet exposed to a first environment and an outlet exposed to a second environment, wherein each outlet is sealed from the first environment at an interface with at least one of the inner surface of the manifold and the outer surface of the PCB.

In an Example 32, the sampling device of Example 31, the one or more pumping elements comprising one or more ultrasonic micropumps.

In an Example 33, the sampling device of any of Examples 26-32, wherein the at least one airflow channel comprises a primary airflow channel, the manifold comprising: an interface surface configured to mate with an interface portion of the outer surface of the PCB; and at least one inner channel surface defining the primary airflow channel.

In an Example 34, the sampling device of Example 33, the manifold further comprising at least one additional inner surface configured to partially define at least one secondary airflow channel, wherein the at least one secondary airflow channel is configured to provide airflow to an inlet of a mass flow sensor, the mass flow sensor comprising an outlet that opens into an ambient environment having an ambient air pressure, and wherein the mass flow sensor is configured to obtain measurements to facilitate estimation of at least one of a pressure drop across a sampling filter and an aerosol mass accumulation rate onto a sampling filter, the ambient environment comprising at least one of the inner chamber and an environment outside of the housing.

In an Example 35, the sampling device of any of Examples 19-34, further comprising an optical sensor for determining one or more air quality parameters.

In an Example 36, the sampling device of any of Examples 19-35, further comprising an airflow path, wherein the airflow path does not include tubing.

In an Example 37, a portable, size-selective aerosol sampling device, comprising: a housing at least partially enclosing an inner chamber, the housing comprising a size-selective inlet; an airflow assembly disposed within the inner chamber, the airflow assembly comprising: an airflow channel; and one or more ultrasonic micropumps configured to generate a flow of air within the airflow channel.

In an Example 38, the sampling device of Example 37, the airflow assembly comprising: a portion of a printed circuit board (PCB); and a manifold configured to be sealably coupled to the portion of the PCB to define at least one airflow channel disposed between an inner surface of the manifold and an outer surface of the PCB.

In an Example 39, the sampling device of Example 38, wherein the manifold comprises a plurality of inside surfaces of the upper housing portion or the lower housing portion.

In an Example 40, the sampling device of Example 38, wherein the manifold comprises a monolithic part created using at least one of an injection-molding process, a three-dimensional printing process, and a machining process.

In an Example 41, the sampling device of any of Examples 38-40, wherein a seal between the manifold and the PCB is achieved using at least one of an adhesive and a compressible gasket.

In an Example 42, the sampling device of any of Examples 38-41, further comprising one or more sensors mounted to the outer surface of the PCB and disposed between the inner surface of the manifold and the outer surface of the PCB.

In an Example 43, the sampling device of any of Examples 37-42, each of the one or more pumping elements having an inlet exposed to a first environment and an outlet exposed to a second environment, wherein each outlet is sealed from the first environment at an interface with at least one of the inner surface of the manifold and the outer surface of the PCB.

In an Example 44, the sampling device of any of Examples 37-43, the one or more pumping elements comprising one or more ultrasonic micropumps.

In an Example 45, the sampling device of any of Examples 38-44, wherein the at least one airflow channel comprises a primary airflow channel, the manifold comprising: an interface surface configured to mate with an interface portion of the outer surface of the PCB; and at least one inner channel surface defining the primary airflow channel.

In an Example 46, the sampling device of Example 45, the manifold further comprising at least one additional inner surface configured to partially define at least one secondary airflow channel, wherein the at least one secondary airflow channel is configured to provide airflow to an inlet of a mass flow sensor, the mass flow sensor comprising an outlet that opens into an ambient environment having an ambient air pressure, and wherein the mass flow sensor is configured to obtain measurements to facilitate estimation of at least one of a pressure drop across a sampling filter and an aerosol mass accumulation rate onto a sampling filter, the ambient environment comprising at least one of the inner chamber and an environment outside of the housing.

In an Example 47, the sampling device of any of Examples 37-46, wherein the size-selective inlet comprises at least one of an impactor, a filter, a cyclone and an inhalable inlet.

In an Example 48, the sampling device of any of Examples 37-47, further comprising an optical sensor for determining one or more air quality parameters.

In an Example 49, the sampling device of any of Examples 37-48, comprising an airflow path, wherein the airflow path does not include tubing.

In an Example 50, the sampling device of any of Examples 37-49, further comprising a sampling assembly having a coupling interface configured to be removably mated with a corresponding coupling interface of the sampling assembly receiver, the sampling assembly comprising a cyclone assembly, the cyclone assembly comprising: a cyclone body having an at least partially conical cavity defined therein, wherein the cavity extends from a lower end of the cyclone body toward an upper end of the cyclone body; a cyclone inlet aperture defined through the cyclone body; a cyclone floor disposed adjacent the lower end of the cyclone body; and a size-selective cyclone outlet aperture defined through the cyclone floor.

In an Example 51, the sampling device of Example 50, the sampling assembly further comprising a filter cartridge comprising a filter cartridge housing configured to house a sampling filter, the filter cartridge housing comprising: a filter cartridge base configured to receive the sampling filter; and a filter cartridge cap detachably coupled to the filter cartridge base, wherein an upper surface of the filter cartridge cap comprises the cyclone floor.

In an Example 52, the sampling device of either of Examples 50 or 51, wherein characteristics of the size-selective cyclone are configured to allow particulate matter having a selection size to pass through the size-selective cyclone outlet aperture for deposition on a sampling filter, wherein the selection size comprises at least one of an aerodynamic diameter of between approximately 1.0 microns and approximately 10.0 microns, Respirable PM, Thoracic PM, and Inhalable PM.

In an Example 53, the sampling device of any of Examples 37-52, further comprising: a first automatic-identification (AID) component associated with the sampling assembly; and a second AID component associated with the housing, wherein the first and second AID components are configured to communicate using an AID technique, the AID technique comprising at least one of an electronic-contact identification technique, a near-field communication (NFC) technique, and a radio-frequency identification (RFID) technique.

In an Example 54, the sampling device of any of Examples 50-53, the sampling assembly further comprising a sampling assembly skirt disposed around at least a portion of an outside surface of the cyclone body, the sampling assembly skirt comprising: an upper wall having an upper surface that is at least approximately perpendicular to a central vertical axis of the cyclone body; and a side wall extending downward from a lower surface of the upper wall, wherein an outside surface of the side wall is configured to mate with an inner surface of the sampling assembly receiver, wherein the upper surface of the upper wall and an inner surface of the side wall at least partially define a screening chamber into which air is configured to flow before entering the cyclone, and wherein the upper wall includes at least one inlet aperture extending between the upper surface of the upper wall and the lower surface of the upper wall, configured to provide an airflow pathway between an external environment and the screening chamber.

In an Example 55, the sampling device of Example 54, further comprising one or more water-release apertures defined through the sampling assembly receiver and configured to facilitate drainage of water from the screening chamber.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIGS. 1D-1H are various views of a sampling assembly, in accordance with embodiments of the subject matter disclosed herein.

FIGS. 1I-1L are various views of an airflow assembly, in accordance with embodiments of the subject matter disclosed herein.

FIGS. 2A and 2B are exploded, perspective views of a portable, size-selective aerosol sampling device, in accordance with embodiments of the subject matter disclosed herein.

FIGS. 3A and 3B are perspective views of a portable, size-selective aerosol sampling device, in accordance with embodiments of the subject matter disclosed herein.

FIG. 3D is an exploded, perspective view of the portable, size-selective aerosol sampling device of FIGS. 3A-3C, in accordance with embodiments of the subject matter disclosed herein.

FIGS. 3E-3I are various views of a sampling assembly, in accordance with embodiments of the subject matter disclosed herein.

FIGS. 3J-3R are various views of an airflow assembly, in accordance with embodiments of the subject matter disclosed herein.

Figure 1A:
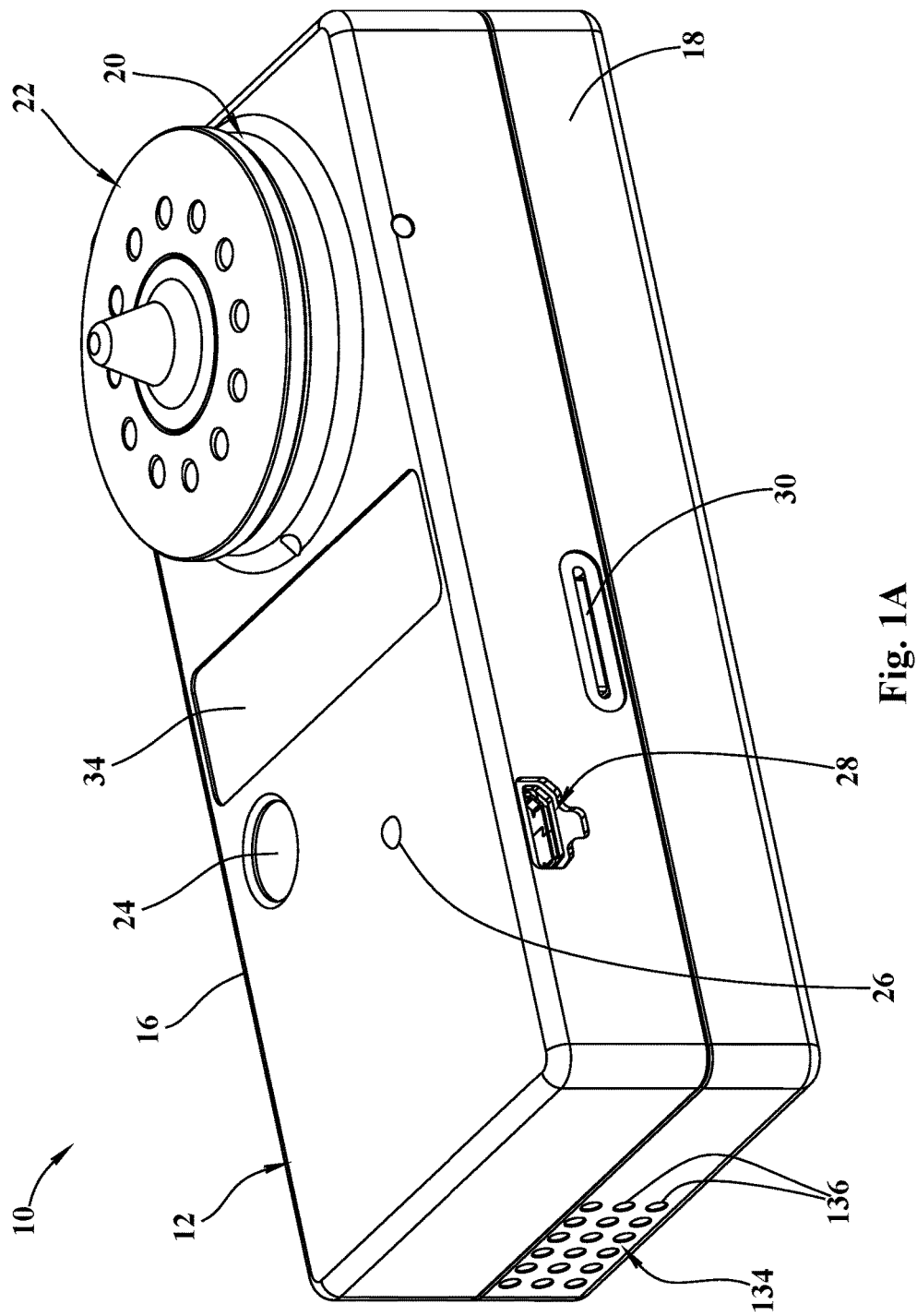
FIG. 1A is a perspective view of a portable, size-selective aerosol sampling device, in accordance with embodiments of the subject matter disclosed herein.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

DETAILED DESCRIPTION

Embodiments of the disclosed subject matter include portable, size-selective aerosol sampling devices having ultrasonic piezoelectric micropumps. Embodiments of the sampling device permit collection of particulate matter from various microenvironments. Samples collected using embodiments of the device can be subsequently processed and used to generate information regarding air quality and characteristics (e.g., pollutants), which may be used, for example, to establish risk assessment studies.

Embodiments of the present disclosure take advantage of recent advances in consumer electronics, open-source software platforms, and additive manufacturing to develop portable and wearable aerosol samplers. In accordance with these embodiments, the present disclosure provides a sampling device that is compact, lightweight, and quieter than many conventional devices when running. Throughout this disclosure, the term "aerosol" can mean any combination of particles of any size and gas of any type such as, for example, a colloid, a suspension, and/or the like. While this disclosure discusses using the sampling device to characterize particles in an aerosol, embodiments of the sampling device may also, or alternatively, be used to characterize particles in other fluid media including, but not limited to, a liquid, a plasma, and/or the like. Further, the sampling device may characterize particles by detecting the particles, counting the particles, determining sizes (e.g., aerodynamic diameters) of particles, measuring a size distribution of particles, determining a composition of particles, determining a particle type distribution, and/or the like.

According to embodiments, the sampling device may be constructed having an airflow path from a size-selective inlet to a device outlet, without using any tubing. The size-selective inlet may include at least one of an impactor, a filter, a cyclone, an inhalable inlet, and/or the like. In embodiments, the device includes a sampling assembly configured to be removably coupled directly to a sampling device housing (e.g., without using tubing), and an airflow assembly that may be constructed without using tubing. For example, embodiments of the airflow assembly include a manifold that is sealably coupled to a surface of a printed circuit board (PCB), defining an airflow path therebetween. In embodiments, the sampling device may include tubing to couple one or more of the components.

Embodiments of the sampling device include a time-integrated filter sampler that utilizes an ultrasonic piezoelectric micropump to drive airflow (as opposed to a traditional diaphragm pump). In embodiments, the micropump operates by converting electric charge into reversible mechanical expansion of a ceramic crystal at high-frequency (e.g., at approximately ~25 kHz). Air is expelled from a miniature chamber below the crystal and through a diffuser nozzle, which functions as a passively-dynamic valve, preventing backflow. Without a traditional check valve, piezoelectric micropumps are not as susceptible to damage from dirty/multiphase flow; further, without any sliding interfaces, piezoelectric micropumps operate at higher efficiency, and with less noise, than many conventional devices.

Figure 1B:
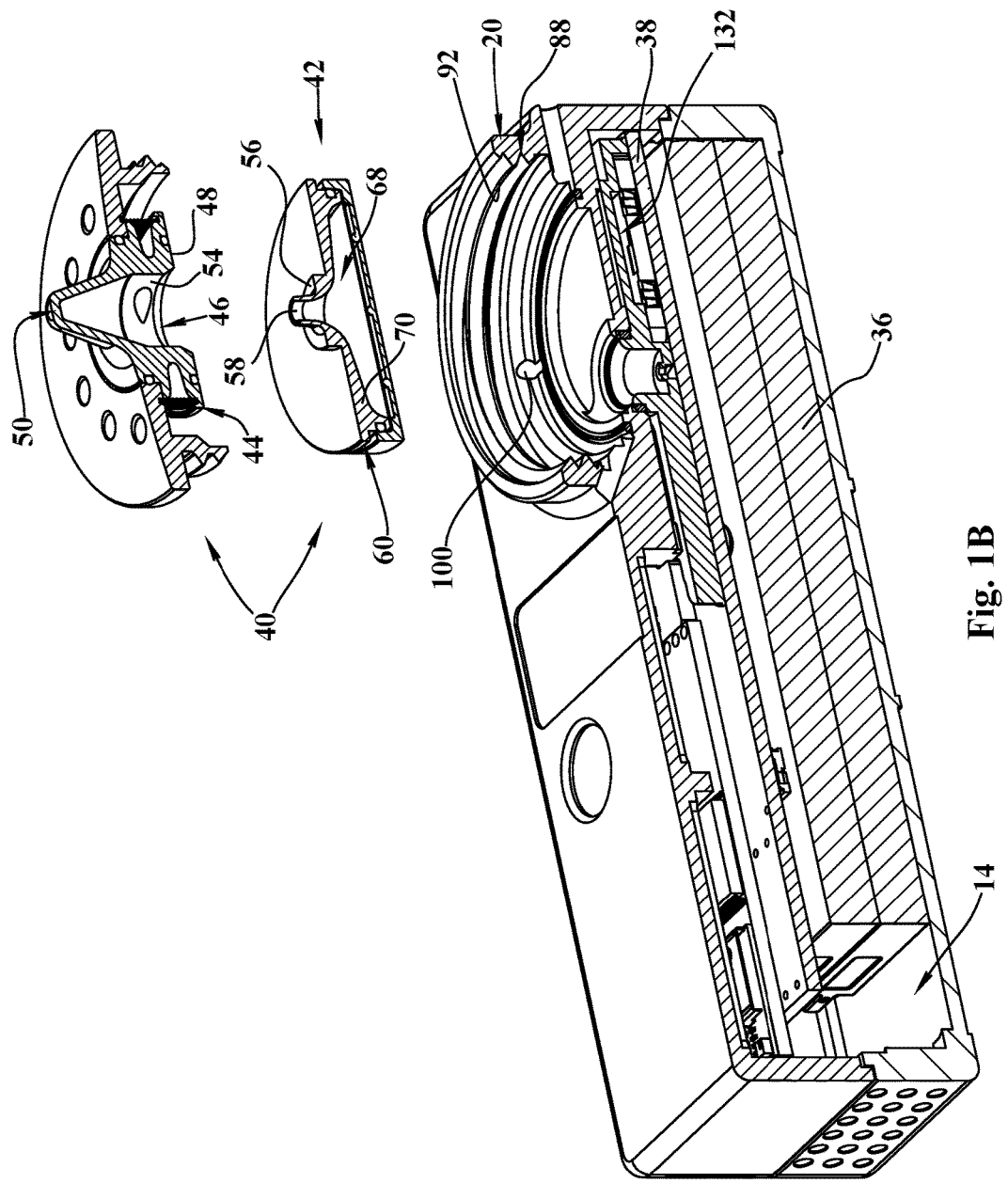
FIG. 1B is an exploded, perspective cross-sectional view of the portable, size-selective aerosol sampling device of FIG. 1A, in accordance with embodiments of the subject matter disclosed herein.
Figure 1C:
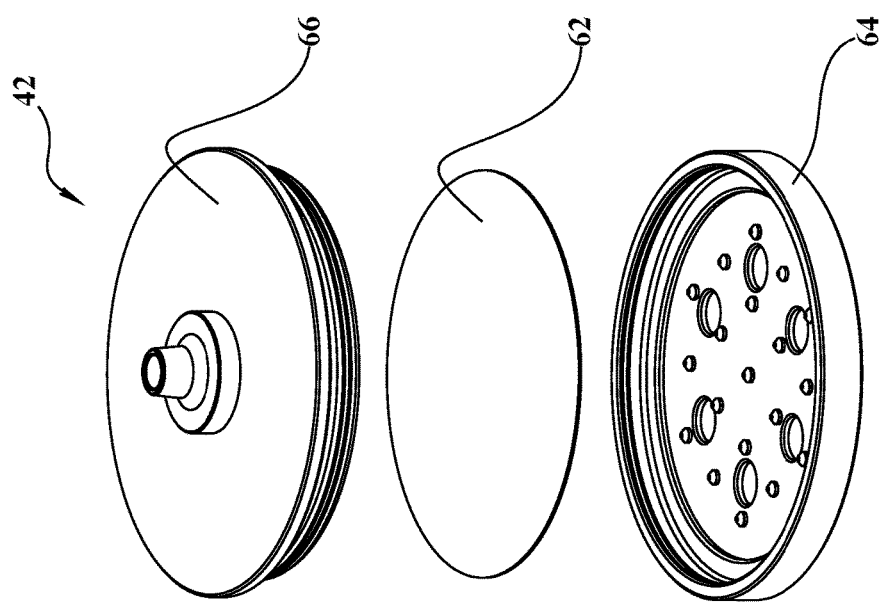
FIG. 1C is an exploded, perspective view of a filter cartridge, in accordance with embodiments of the subject matter disclosed herein.

FIG. 1A depicts an illustrative portable size-selective aerosol sampling device 10, in accordance with embodiments of the disclosed subject matter; and FIG. 1B is an exploded cross-sectional perspective view of the illustrative sampling device 10 depicted in FIG. 1A, in accordance with embodiments of the subject matter disclosed herein. As shown, the sampling device 10 includes a housing 12 at least partially enclosing an inner chamber 14. The housing 12 includes an upper housing portion 16 and a lower housing portion 18, configured to be coupled together to form the housing 12. The housing 12 further includes a sampling assembly receiver 20 configured to receive a sampling assembly 22. The sampling device 10 includes an input/output (I/O) device 24, which may be, for example, a button and/or light indicator. The sampling device 10 may include another I/O device 26 such as, for example, a light indicator.

As shown in FIG. 1A, the sampling device 10 also includes a communication and/or charging port 28 (e.g., a universal serial bus (USB) port, a micro-USB port, etc.) and a secure digital (SD) card port 30. Additionally, as shown in FIG. 1A, the sampling device 10 may include a label region 34 configured to receive a label for automatic identification (AID), manual identification, and/or the like. The label may be applied to the label region 34 via adhesive, printing, etching, and/or the like, and may include, for example, characters (e.g., a name, handwritten identifiers, printed identifiers, etc.), a bar code, a matrix code (e.g., an Aztec code, a data matrix, a quick response (QR) code, etc.), and/or the like. Within the inner chamber 14, the sampling device 10 includes a power source 36 and a printed circuit board (PCB) 38, to which any number of functional components may be operably coupled. The PCB 38, as well as other electrical components of the sampling device 10, is powered by the power source 36, which is illustrated as a battery pack. In embodiments, the power source 36 can include rechargeable battery cells such as, for example, lithium ion battery cells. The power source 36 may also, or alternatively, include rectifiers, capacitors, acoustic transducers, photovoltaic cells, and/or the like.

As depicted in FIGS. 1A and 1B, and in FIGS. 1C-1H, which depict various aspects of the sampling assembly 22, the sampling assembly 22 includes a cyclone assembly 40 and a filter cartridge 42. The cyclone assembly 40 includes a cyclone body 44 having an at least partially conical cavity 46 defined therein. The cavity 46 extends from a lower end 48 of the cyclone body 44 toward an upper end 50 of the cyclone body 44. A cyclone inlet aperture 52 is defined through the cyclone body 44, exiting tangentially to the inside surface 54 of the cyclone body 44 to impart a rotational characteristic to airflow entering the cavity 46. A cyclone floor 56 is configured to be disposed adjacent the lower end 48 of the cyclone body 44; and a size-selective cyclone outlet 58 is defined through the cyclone floor 56.

The filter cartridge 42 includes a filter cartridge housing 60 configured to house a sampling filter 62. The filter cartridge housing 60 includes a filter cartridge base 64 configured to receive the sampling filter 62, and a filter cartridge cap 66 configured to be detachably coupled to the filter cartridge base 64. As shown, the cyclone floor 56 may be at least a portion of the upper surface of the filter cartridge cap 66. As such, the size-selective cyclone outlet 58 opens into a sampling chamber 68 between the sampling filter 62 and a lower surface 70 of the filter cartridge cap 66.

According to embodiments, characteristics of the size-selective cyclone are configured to allow particulate matter having a selection size to pass through the size-selective cyclone outlet aperture for deposition on a sampling filter. The selection size may include, for example, an aerodynamic diameter of between approximately 1.0 microns and approximately 10.0 microns, Respirable PM, Thoracic PM, Inhalable PM, and/or the like. In embodiments, the characteristics may include, for example, the diameter of the size-selective cyclone outlet aperture, one or more diameters of the cyclone cavity, length of the cyclone cavity, angle of cyclone cavity walls with respect to a central axis, airflow rate, and/or the like.

As shown, the sampling assembly 22 includes a sampling assembly skirt 72 disposed around at least a portion of an outside surface 74 of the cyclone body 44. The sampling assembly skirt 72 includes an upper wall 76 having an upper surface 78 that is at least approximately perpendicular to a central vertical axis 80 of the cyclone body 44. A side wall 82 extends downward from a lower surface 84 of the upper wall 76. The outside surface 86 of the side wall 82 includes a coupling interface of the side wall 82 configured to removably mate with a corresponding coupling interface 88 of a sampling device receiver 20 defined in the upper housing portion 16. As shown, for example, the coupling interface may be configured to mate with an inner surface 92 of the sampling assembly receiver 20 such as, for example, by coupling corresponding threads together.

When the sampling assembly 22 is assembled, at least a portion of the lower surface 84 of the upper wall 76 and at least a portion of an inner surface 94 of the side wall 82 at least partially define a screening chamber 96 into which air is configured to flow before entering the cyclone assembly 40. The upper wall 76 of the sampling assembly skirt 72 includes inlet apertures 98 extending between the upper surface 78 of the upper wall 76 and the lower surface 84 of the upper wall 78. The inlet apertures 98 are configured to provide an airflow pathway between an external environment and the screening chamber 96. One or more water-release apertures 100 may be defined through the sampling assembly receiver 20 and/or the upper housing portion 16, and may be configured to facilitate drainage of water from the screening chamber 96. A coarse screen 101 may be disposed within the screening chamber 96 and may be configured to prevent dirt and/or other particles that are larger than particles that the sampling device 10 is configured to sample from entering the cyclone assembly 40. For example, grooves 102 may be defined in the lower surface 84 of the upper wall 76 and the outside surface 74 of the cyclone body 44, where the grooves 102 are configured to hold the screen 101 in place.

In embodiments, the sampling assembly skirt 72 may be configured to be detachably coupled to the cyclone body 44 via any number of different coupling techniques. As shown, for example, the sampling assembly skirt 72 may be configured to be detachably coupled to the cyclone body 44 via an interference fit facilitated by an O-ring 104 disposed between the outside surface 74 of the cyclone body and an inside surface 106 of the upper wall 76 of the sampling assembly skirt 72. In embodiments, other coupling techniques may be used to detachably couple the cyclone body 44 to the sampling assembly skirt 72.

Additionally, as shown, an air flow path 108 through the sampling assembly 22 may be facilitated, in part, by sealing the filter cartridge cap 66 to the filter cartridge base 64 such as, for example, by coupling the filter cartridge cap 66 to the filter cartridge base 64 using an interference fit facilitated by an O-ring 110 disposed between an outside surface 112 of a side wall 114 of the filter cartridge cap 66 and an inside surface 116 of a side wall 118 of the filter cartridge base 64. To further facilitate achieving the airflow 108, the cyclone floor 56 may be sealed to the cyclone body 44 via an O-ring 120 disposed between a lower surface 122 of the cyclone body 44 and the cyclone floor 56. Similarly, the filter cartridge 42 may be sealed to a floor 124 of the sampling assembly receiver 20 via an o-ring 126 disposed between a lower surface 128 of a lower wall 130 of the filter cartridge 42 and the floor 124 of the sampling assembly receiver 20. In this manner, the airflow through the sampling device, including the portion of the path from the sampling assembly to the airflow assembly, can be created without using any tubing, which may facilitate reduced materials costs, labor costs, and enable reduction of the size of the device.

When the sampling assembly 22 is coupled to the sampling device housing 12, and when the device is active, air enters the sampling assembly 22 and exits through the lower wall 130 of the filter cartridge 42 and enters an airflow assembly 132 disposed within the inner chamber 14 of the sampling device 10. As shown, the airflow assembly 132 includes a portion of an airflow path from the size-selective inlet (e.g., the cyclone assembly 40) through the sampling device 10 to an airflow outlet 134 of the sampling device 10. As shown in FIG. 1A, the airflow outlet 134 may include a set of outlet apertures 136 defined in the housing 12.

As shown in FIGS. 1I-1L, the airflow assembly 132 includes a portion of the PCB 38 and a manifold 138 that is configured to be sealably coupled to the portion of the PCB 38 to define at least one airflow channel 140 disposed between an inner surface 142 of the manifold 138 and an outer surface 144 of the PCB 38. The seal, at an interface surface 146 of the manifold 138 and a corresponding interface portion (not shown) of the PCB 38 may be achieved using at least one of an adhesive and a compressible gasket. In this manner, the airflow assembly can be created without using any tubing, which may facilitate reduced materials costs, labor costs, and enable reduction of the size of the device.

In embodiments, as shown, the at least one airflow channel includes a primary airflow channel 140 defined by at least one inner channel surface 148. The manifold 138 may further include at least one additional inner surface 150 configured to at least partially define at least one secondary airflow channel 152. In embodiments, a secondary airflow channel 152 is configured to provide airflow to a sensor such as, for example, a flow sensor 154. One of more sensors (not shown) may be mounted to the PCB 38. In embodiments, for example, the sensors may include one or more surface-mounted devices (SMDs) configured to obtain measurements associated with one or more operational and/or environmental parameters. According to embodiments, sensors that are mounted within the airflow path (e.g., between an inside surface of a manifold and the upper surface of the PCB) may include gas composition sensors (e.g., for detecting carbon monoxide, volatile organic carbon species, methane, nitrogen oxides, ozone, hydrogen sulfide, relative humidity, absolute humidity, etc.), environmental sensors (e.g., for determining temperature, pressure, air velocity, etc.), mass flow sensors, and/or the like. Embodiments may include any number of other sensors mounted to the PCB but not within the airflow path such as, for example, gas composition sensors, environmental sensors, radio-frequency sensors (e.g., GPS, antennas, etc.), radioactivity sensors, sun photometry sensors (e.g., for sensing light intensity at a specified wavelength), and/or the like.

One or more pumping elements 156 may be configured to be disposed adjacent the primary airflow channel 140. In embodiments, each pumping element 156 includes an inlet 158 (or inlets, as is the case, for example in some ultrasonic micropumps, in which fluid can enter the micropump through any number of different locations) exposed to a first environment (e.g., the primary airflow channel 140) and an outlet 160 exposed to a second environment (e.g., the inner chamber 14 of the sampling device 10), where each outlet 160 is isolated from the first environment 140 at a sealed interface with the outer surface 144 of the PCB 38. In other embodiments, the outlet 160 of one or more of the pumping elements 156 may be isolated from the first environment 140 at a sealed interface with the inner channel surface 148 of the manifold 138. The pumping elements 156 may include any number of different types of pumping elements configured to provide an airflow. In embodiments, one of more of the pumping elements 156 include an ultrasonic micropump. Ultrasonic micropumps may include, for example, piezoelectric microblowers manufactured by Murata Manufacturing Co., Ltd. of Japan.

According to embodiments, multiple pumping elements may be configured in a "parallel" arrangement, in which adjacent pumping elements all pull air from a common volume and discharge air into another common volume; or in a "series" arrangement, in which a pump discharges air into an intermediate volume from which an adjacent pump pulls the air. In embodiments employing pumping elements that include inlets and outlets that can be connected, an outlet of a first pumping element may be directly coupled to an inlet of a second, adjacent pumping element. In embodiments, the "parallel" configuration may be used to facilitate increasing flow rate at a given pressure/load, while the "series" configuration may be used to facilitate increasing pressure capability for a given pressure/load. According to embodiments, sets of pumping elements may be arranged according to the "parallel" configuration, the "series" configuration, and/or a combination thereof. These configurations may be chosen and tuned to facilitate targeting specific flow/resistance operating points. In embodiments, these configurations may be adjusted using variations in the manifold flow pathway routing, by passing air through the PCB to route it to a subsequent pumping element, and/or the like. According to embodiments, rather than positioning pumping elements on the PCB, pumping elements may be positioned such that they are connected only to an edge of the PCB, e.g., via electrical contacts. In this manner, additional flexibility regarding the positioning of the pumping element may be achieved such that the pumping elements may be sealed to any other structure (e.g., a housing portion, another manifold, etc.) of the device.

The illustrative sampling device 10 shown in FIGS. 1A-1L is not intended to suggest any limitation as to the scope of use or functionality of embodiments of the present disclosure. Neither should the illustrative sampling device 10 be interpreted as having any dependency nor requirement related to any single component or combination of components illustrated therein. Additionally, various components depicted in FIGS. 1A-1L may be, in embodiments, integrated with various ones of the other components depicted therein (and/or components not illustrated), all of which are considered to be within the ambit of the present disclosure. For example, while the manifold is illustrated as being a monolithic structure in the above figures, the manifold may be integrated into the housing of the sampling device. Thus, for example, a housing portion and the manifold may be manufactured as a single piece.

FIGS. 2A and 2B are exploded perspective views of a portion of a portable, size-selective aerosol sampling device 162, in which the manifold is integrated into the housing, in accordance with embodiments of the subject matter disclosed herein. As shown, the sampling device 162 includes an upper housing portion 164 and a lower housing portion 166. A set of inside surfaces 168 of the upper housing portion 164 define a manifold 170. As with the manifold described above with regard to FIGS. 1A-1L, the manifold 170 is configured to be sealably coupled to a portion of an upper surface 172 of a PCB 174.

According to embodiments, the manifold 170 may be similar to the manifold 138 described above and depicted in FIGS. 1I-1K, and may define a primary airflow channel 176 and a secondary airflow channel 178. Additionally, a set of pumping elements 180 may be coupled to the PCB 174 and disposed adjacent the primary airflow channel 176. A flow sensor 182 may be mounted to the PCB 174 and associated with the secondary airflow channel 178. According to embodiments, the manifold 170 may be sealed to the upper surface 172 of the PCB 174, enclosing the pumping elements 180 and sensor 182 within an airflow path. In embodiments, since the manifold 170 may be defined by inner surfaces of the lower housing portion, the sampling device 162 may be manufactured without the necessity of manufacturing a monolithic manifold 170, thus potentially facilitating reducing manufacturing cost and time.

The illustrative sampling device 162 shown in FIGS. 2A and 2B is not intended to suggest any limitation as to the scope of use or functionality of embodiments of the present disclosure. Neither should the illustrative sampling device 162 be interpreted as having any dependency nor requirement related to any single component or combination of components illustrated therein. Additionally, various components depicted in FIGS. 2A and 2B may be, in embodiments, integrated with various ones of the other components depicted therein (and/or components not illustrated), all of which are considered to be within the ambit of the present disclosure.

Figure 3C:
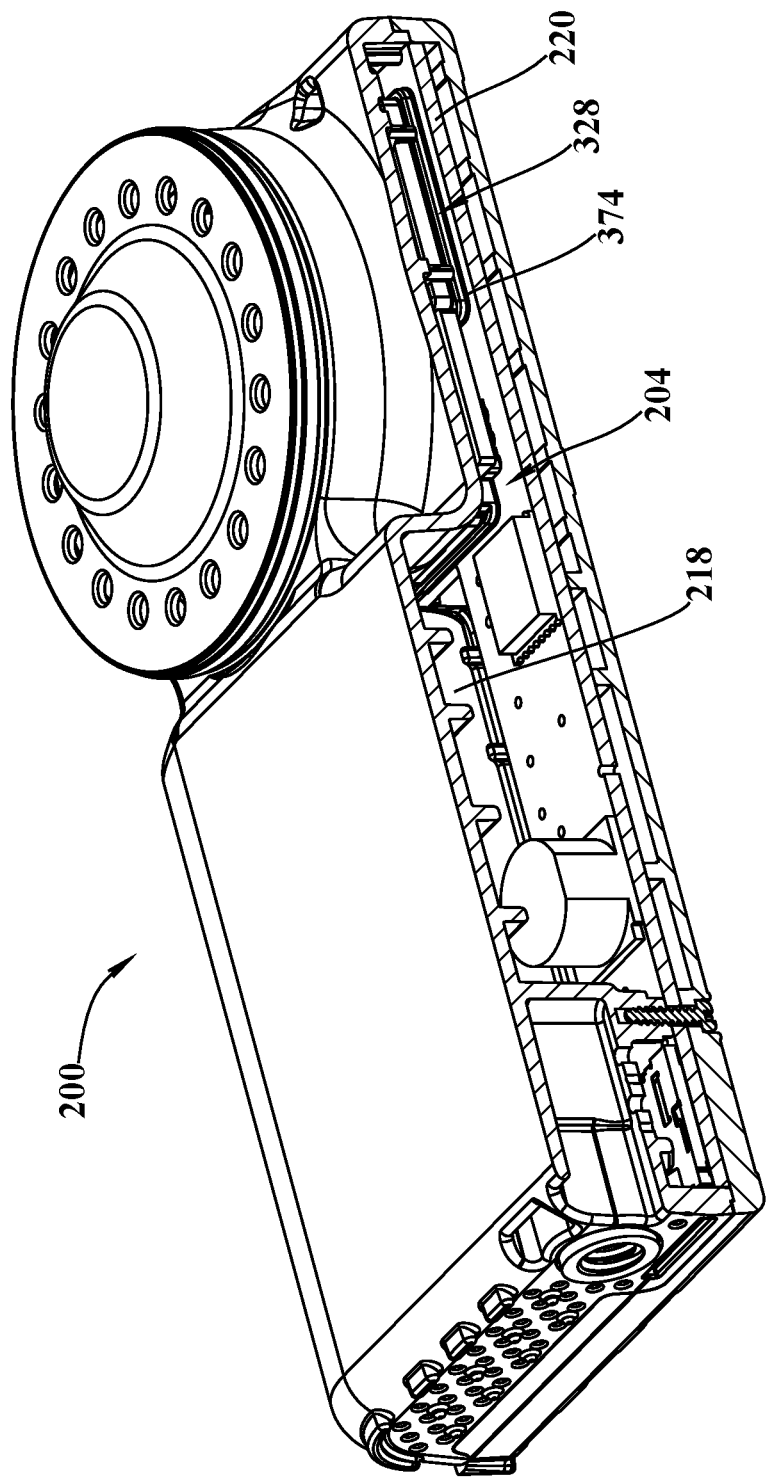
FIG. 3C is a perspective cross-sectional view of the portable, size-selective aerosol sampling device of FIGS. 3A and 3B, in accordance with embodiments of the subject matter disclosed herein.
Figures 3D, 3E:
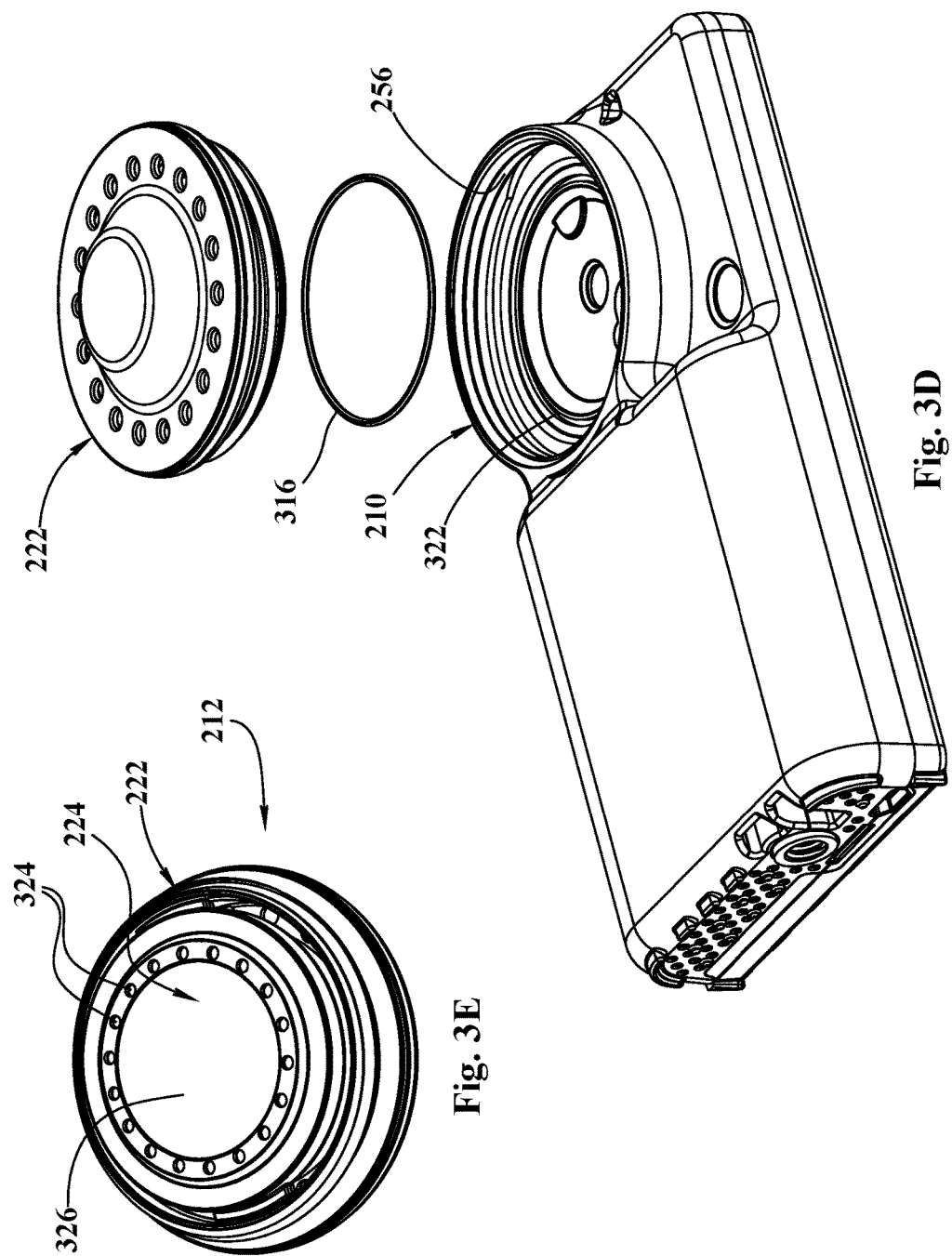
Figure 3I:
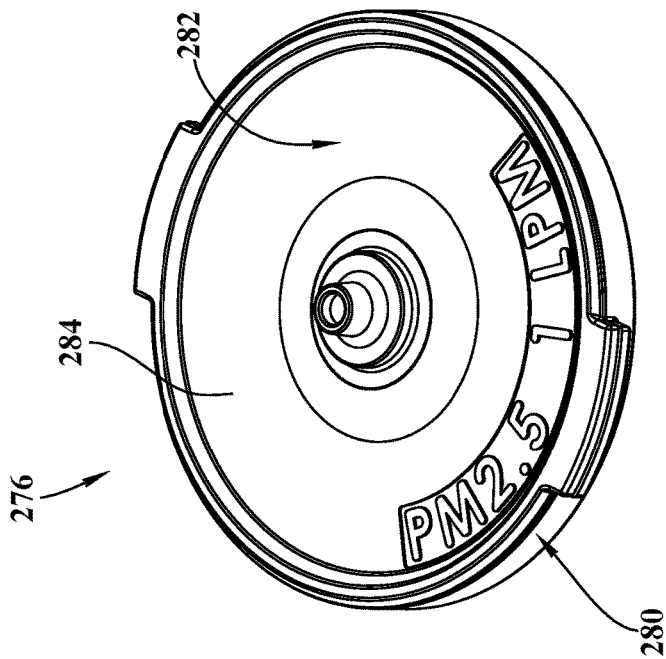
Figure 3H:
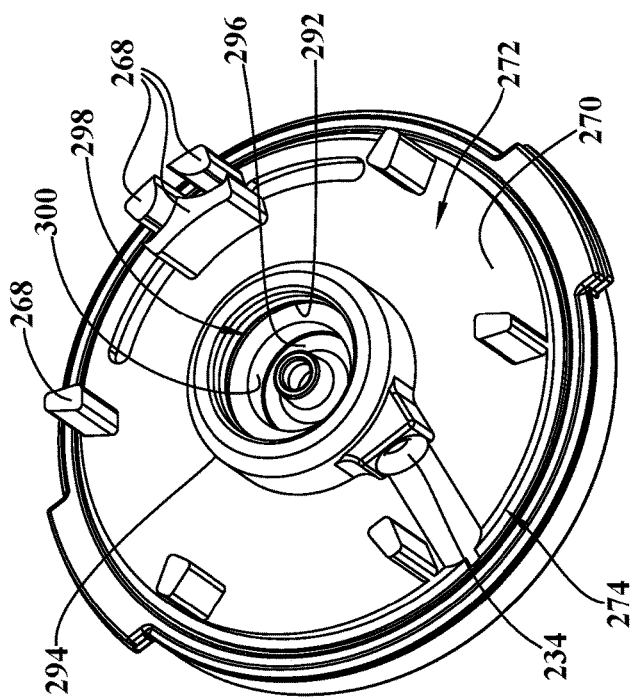
Figure 3K:
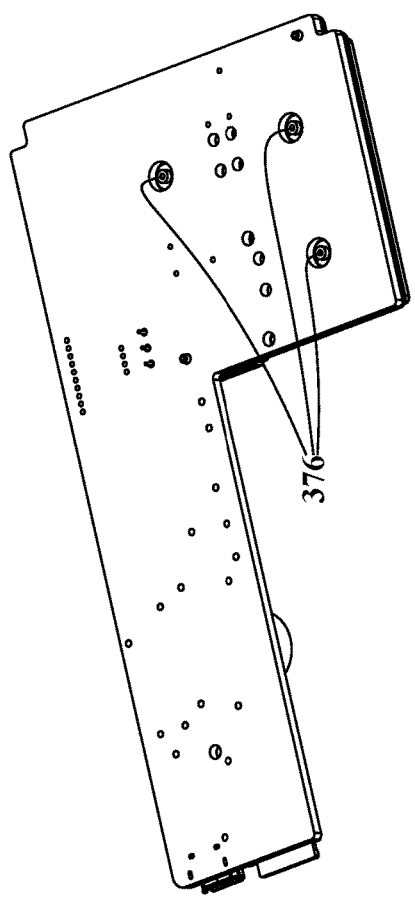
Figure 3J:
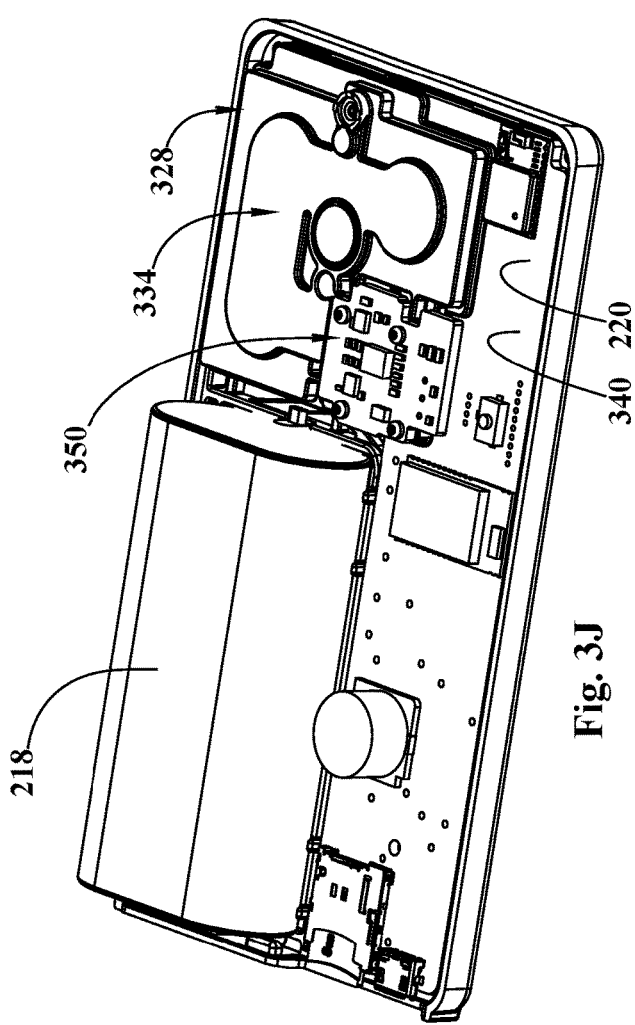
Figure 3L:
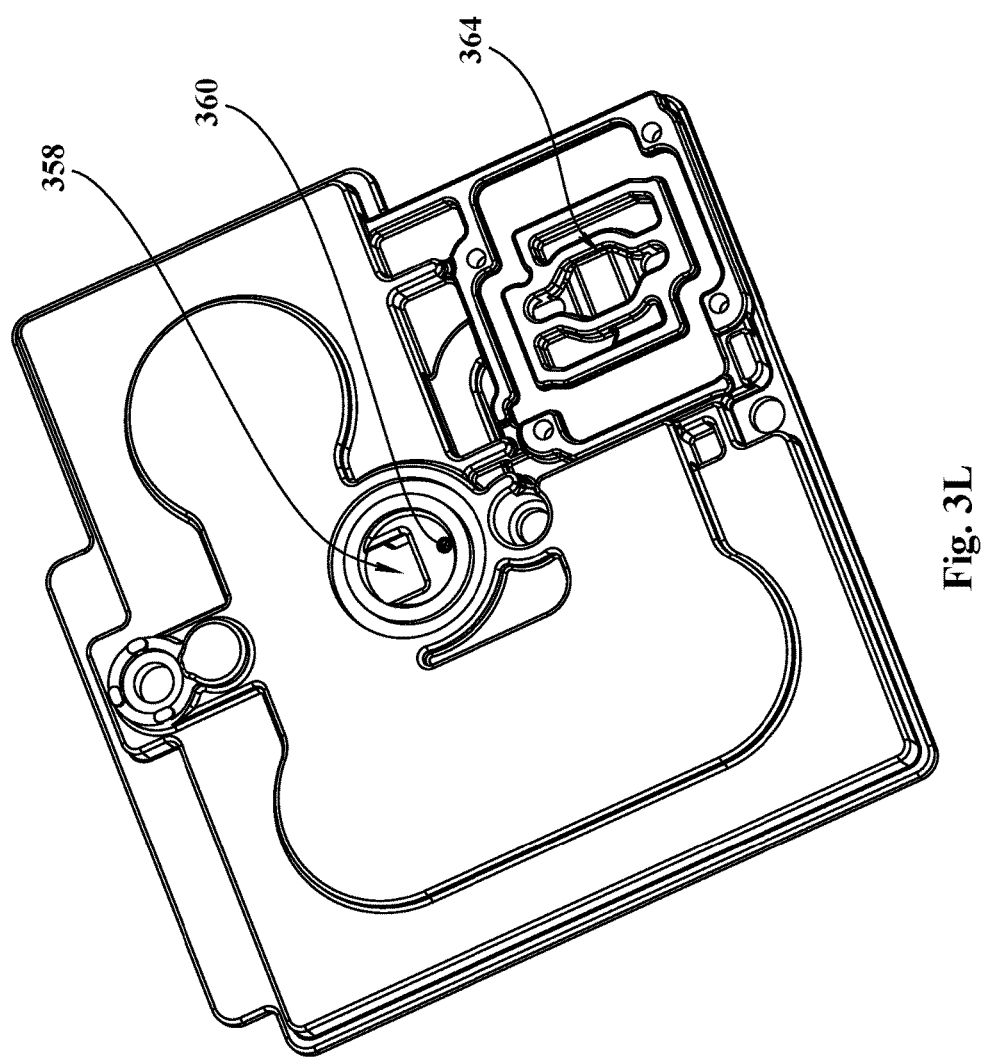
Figure 3M:
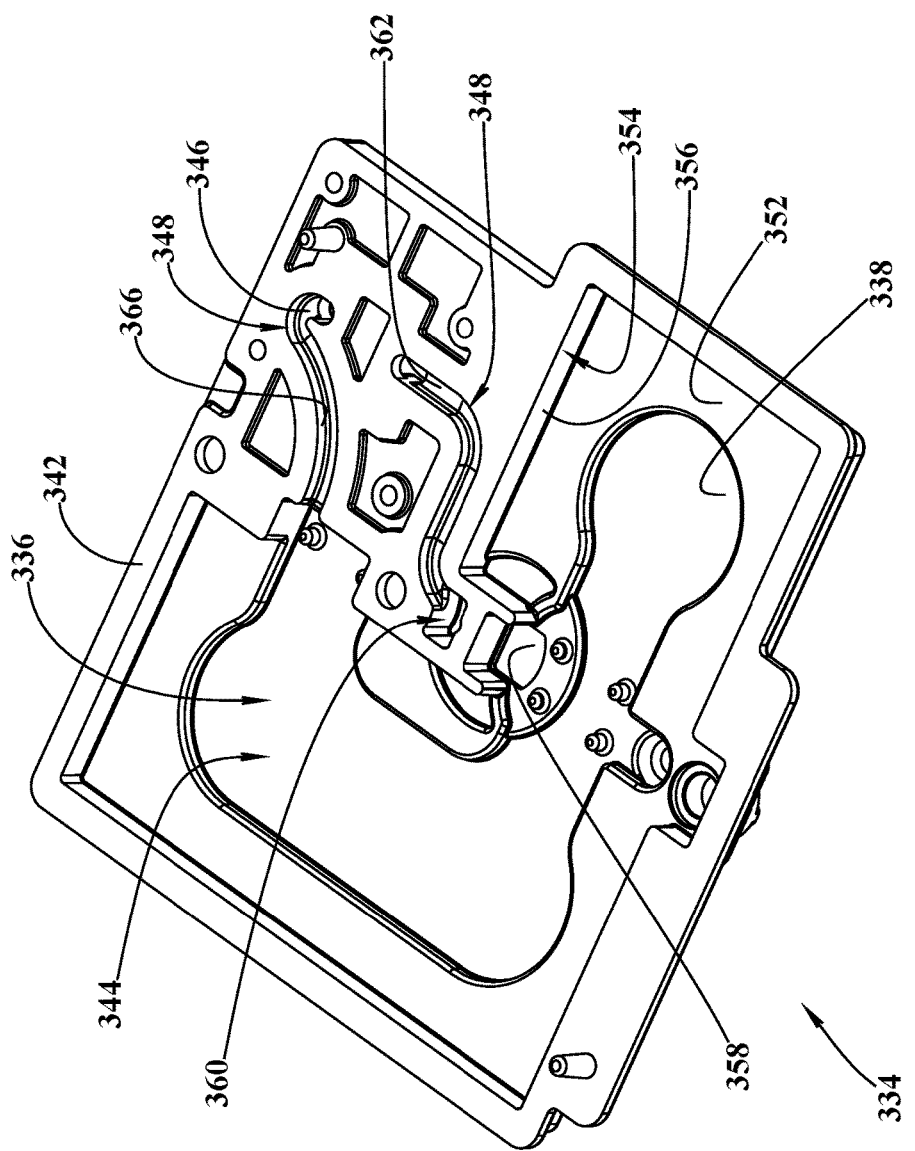

FIGS. 3A-3R depict various aspects of a portable, size-selective aerosol sampling device 200, in accordance with embodiments of the subject matter disclosed herein. As shown, the sampling device 200 includes a housing 202 at least partially enclosing an inner chamber 204. The housing 202 includes an upper housing portion 206 and a lower housing portion 208, configured to be coupled together to form the housing 202. The housing 202 further includes a sampling assembly receiver 210 configured to receive a sampling assembly 212. The sampling device 200 includes an input/output (I/O) device 214, which may be, for example, a button and light indicator.

As shown in FIG. 3A, the sampling device 200 also includes a communication and/or charging port 216A (e.g., a universal serial bus (USB) port, a micro-USB port, etc.), a secure digital (SD) card port 216B, and a support-structure port 216C (e.g., a port configured to facilitate coupling the sampling device 200 to a tripod). Additionally, as shown in FIG. 3B, the sampling device 200 may include a mounting assembly 216D configured to be coupled to a corresponding mount such as, for example, a wearable mount, a wall mount, a dashboard mount, and/or the like. Within the inner chamber 204, the sampling device 200 includes a power source 218 and a printed circuit board (PCB) 220, to which any number of functional components may be operably coupled.

The sampling assembly 212 includes a cyclone assembly 222 and a filter cartridge 224. The cyclone assembly 222 includes a cyclone body 226 having an at least partially conical cavity 228 defined therein. The cavity 228 extends from a lower end 230 of the cyclone body 226 toward an upper end 232 of the cyclone body 226. A cyclone inlet aperture 234 is configured to facilitate providing airflow to the cyclone cavity 228, exiting tangentially to the inside surface 236 of the cyclone body 226 to impart a rotational characteristic to airflow entering the cavity 228. A cyclone floor 238 is configured to be disposed adjacent the lower end 230 of the cyclone body 226; and a size-selective cyclone outlet 240 is defined through the cyclone floor 238.

As shown, the sampling assembly 212 includes a sampling assembly skirt 242 disposed around at least a portion of an outside surface 244 of the cyclone body 226. The sampling assembly skirt 242 includes a first upper wall 246A having an upper surface 248A that is at least approximately perpendicular to a central vertical axis 250 of the cyclone body 226. A first side wall 252A, having an outer surface 254A, extends downward from a periphery of the first upper wall 246A to an inner periphery of a second upper wall 246B having an upper surface 248B that is at least approximately parallel to upper surface 248A of the first upper wall 246A. The sampling assembly skirt 242 includes a second side wall 252B extending downward from the second upper wall 246B. The outside surface 254B of the second side wall 252B includes a coupling interface configured to removably mate with a corresponding coupling interface 256 of a sampling device receiver 210 defined in the upper housing portion 206. As shown, for example, the coupling interface 254B may be configured to mate with an inner surface 256 of the sampling assembly receiver 210 such as, for example, by coupling corresponding threads together.

When the sampling assembly 212 is assembled, at least a portion of a lower surface 260A of the first upper wall 246A, at least a portion of an inner surface 260B of the first side wall 252A, at least a portion of a lower surface 260C of the second upper surface 246B, and an inner surface 260D of the second side wall 252B at least partially define a screening chamber 262 into which air is configured to flow before entering the cyclone assembly 222. The second upper wall 246B of the sampling assembly skirt 242 includes inlet apertures 264 extending between the upper surface 248B of the second upper wall 246B and the lower surface 260C of the second upper wall 246B. The inlet apertures 264 are configured to provide an airflow pathway between an external environment and the screening chamber 262. One or more water-release apertures (not shown) may be defined through the sampling assembly receiver 210 and/or the upper housing portion 206, and may be configured to facilitate drainage of water from the screening chamber 262. A coarse screen 266 may be disposed within the screening chamber 262 and may be configured to prevent dirt, insects, and/or other particles that are larger than particles that the sampling device 10 is configured to sample from entering the cyclone assembly 222. For example, screen-coupling features 268 may be disposed on an upper surface 270 of a lower wall 272 of a floor portion 274 of the sampling assembly skirt 242 and may be configured to hold the screen 266 in place.

The filter cartridge 224 includes a filter cartridge housing 276 configured to house a sampling filter 278. The filter cartridge housing 276 includes a filter cartridge base 280 configured to receive the sampling filter 278, and a filter cartridge cap 282 configured to be detachably coupled to the filter cartridge base 280. As shown, the cyclone floor 238 includes at least a portion of the upper surface 284 of the filter cartridge cap 282. As such, the size-selective cyclone outlet 240 opens into a sampling chamber 286 between the sampling filter 278 and a lower surface 288 of the filter cartridge cap 282.

According to embodiments, characteristics of the size-selective cyclone are configured to allow particulate matter having a selection size to pass through the size-selective cyclone outlet aperture for deposition on a sampling filter. The selection size may include, for example, an aerodynamic diameter of between approximately 1.0 microns and approximately 10.0 microns, Respirable PM, Thoracic PM, Inhalable PM, and/or the like. In embodiments, the characteristics may include, for example, the diameter of the size-selective cyclone outlet aperture, one or more diameters of the cyclone cavity, length of the cyclone cavity, angle of cyclone cavity walls with respect to a central axis, airflow rate, and/or the like.

In embodiments, as shown, the sampling assembly skirt 242 may be integrated with the cyclone body 226, which may be configured to be coupled to the floor portion 274 of the sampling assembly skirt 242 via any number of different coupling techniques. As shown, for example, the cyclone body 226 may be configured to be detachably coupled to the floor portion 274 via an interference fit facilitated by an O-ring 290 disposed between the outside surface 244 of the cyclone body 226 and an inside surface 292 of a protrusion 294 extending upward from the upper surface 270 of the lower wall of the floor portion 274 of the sampling assembly skirt 242. The cyclone inlet aperture 234 is defined through the protrusion 294, exiting tangentially to the inside surface 236 of the cyclone cavity 228 to impart a rotational characteristic to airflow entering the cavity 228. The lower end 230 of the cyclone body 226 may be configured to engage a stopping surface 296 disposed within an aperture 298 defined through the protrusion 294. A side wall 300 extends downward from an inner periphery of the stopping surface 296 and is configured to form a portion of the cyclone, as shown, for example, in FIGS. 3F and 3G.

Additionally, an airflow path through the sampling assembly 212 may be facilitated, in part, by sealing the filter cartridge cap 282 to the filter cartridge base 280 such as, for example, by coupling the filter cartridge cap 282 to the filter cartridge base 280 using an interference fit facilitated by an O-ring 302 disposed between an outside surface 304 of a side wall 306 of the filter cartridge cap 282 and an inside surface 308 of a side wall 310 of the filter cartridge base 280. To further facilitate achieving the airflow, the upper surface 284 of the filter cartridge cap 282 may be sealed to the floor portion 274 of the sampling assembly skirt 242 via an O-ring 312 disposed between a lower surface 314 of the floor portion 274 and the upper surface 284 of the filter cartridge cap 282. Similarly, the filter cartridge 224 may be sealed within the sampling assembly receiver 210 via an O-ring 316 disposed between a lower surface 318 of a lower wall 320 of the filter cartridge 224 and a surface 322 within the sampling assembly receiver 210. In this manner, the airflow through the sampling device, including the portion of the path from the sampling assembly to the airflow assembly, can be created without using any tubing, which may facilitate reduced materials costs, labor costs, and enable reduction of the size of the device.

When the sampling assembly 212 is coupled to the sampling device housing 202, and when the device is active, air enters the sampling assembly 212 and exits through one or more apertures 324 defined within a lower wall 326 of the filter cartridge 224 and enters an airflow assembly 328 disposed within the inner chamber 204 of the sampling device 200. The airflow assembly 328 includes a portion of an airflow path from the size-selective inlet (e.g., the cyclone assembly 222) through the sampling device 200 to an airflow outlet 330 of the sampling device 200. As shown in FIG. 3A, the airflow outlet 330 may include a set of outlet apertures 332 defined in the housing 202.

As shown, the airflow assembly 328 includes a portion of the PCB 220 and a manifold 334 that is configured to be sealably coupled to the portion of the PCB 220 to define at least one airflow channel 336 disposed between an inner surface 338 of the manifold 334 and an outer surface 340 of the PCB 220. The seal, at an interface surface 342 of the manifold 334 and a corresponding interface portion (not shown) of the PCB 220 may be achieved using at least one of an adhesive and a compressible gasket. In this manner, the airflow assembly can be created without using any tubing, which may facilitate reduced materials costs, labor costs, and enable reduction of the size of the device. In embodiments, as shown, the at least one airflow channel includes a primary airflow channel 344 defined by at least one inner channel surface 338. The manifold 334 may further include at least one additional inner surface 346 configured to at least partially define at least one secondary airflow channel 348. In embodiments, a secondary airflow channel 348 is configured to provide airflow to a sensor such as, for example, a flow sensor 350.

As shown, the manifold 334 may further include a shelf surface 352 that is approximately parallel to the interface surface 342; and a side wall 354 having an inside surface 356 extending between the interface surface 342 and the shelf surface 352. The inner channel surface 338 (or surfaces) is recessed with respect to the shelf surface 352. Similarly, the additional inner surface 346 is recessed with respect to the interface surface 342. A primary manifold inlet 358 facilitates providing airflow from the sampling assembly 212 to the primary airflow channel 344, and a secondary manifold inlet 360 facilitates providing airflow from the sampling assembly 212 to the secondary airflow channel 348. As shown, the secondary airflow channel 348 may include two portions—a first portion 362 configured to provide airflow from the secondary manifold inlet 360 to a flow sensor interface 364, and a second portion 366 to provide the airflow from the flow sensor interface 364 to the primary airflow channel 344. In embodiments, the flow sensor interface 364 may be configured to receive a flow sensor such as, for example, a functional portion of a D6F-P MEMS flow sensor available from OMRON Corporation of Japan. In embodiments, a flow sensor may be included in a bypass airflow path (e.g., a secondary airflow channel).

In embodiments, the secondary airflow channel 348 may be configured to provide airflow to an inlet of a mass flow sensor (not shown), which may include an outlet that opens into an ambient environment having at least approximately ambient air pressure (e.g., the inner chamber 204, the external environment, etc.). In such embodiments, the mass flow sensor may be configured to obtain measurements to facilitate estimation of at least one of a pressure drop across a sampling filter and an aerosol mass accumulation rate onto a sampling filter. According to embodiments, the mass flow sensor may include an SDP series sensor available from Sensirion AG of Switzerland. In embodiments, the mass flow sensor may be configured so that its outlet does not open to the ambient environment. Instead, the flow sensor may be configured to be an "in-line" sensor, with its inlet and outlet both opening to the secondary flow path. In embodiments, the sensor may be built directly into the PCB during manufacturing of the PCB, which may facilitate reduced cost, manufacturing time, weight, size, and/or the like, and may be installed without accessing an upper surface of the manifold (e.g., in implementations in which the manifold is integrated with an upper housing portion).

As shown in FIGS. 3N-3R, one or more pumping elements 368, 370, 372 may be configured to be disposed adjacent the primary airflow channel 344. In embodiments, each pumping element 368, 370, 372 includes an inlet (not shown) exposed to a first environment (e.g., the primary airflow channel 344) and an outlet 376 exposed to a second environment (e.g., the inner chamber 204 of the sampling device 200), where each outlet 376 is sealed from the first environment 344 at an interface with the upper surface 340 of the PCB 220. The pumping elements 368, 370, 372 may include any number of different types of pumping elements configured to provide an airflow. In embodiments, one or more of the pumping elements 368, 370, 372 include an ultrasonic micropump. Ultrasonic micropumps may include, for example, piezoelectric microblowers manufactured by Murata Manufacturing Co., Ltd. of Japan Although embodiments are depicted as including three micropumps, any number of micropumps may be used to achieve a desired airflow rate and a desired form factor.

According to embodiments, the airflow assembly 328 may be assembled by sealing a manifold assembly 378 to the upper surface 340 of the PCB 220. In other embodiments, the manifold may be integrated within the housing (e.g., defined by inner surfaces of the upper housing portion 206. The manifold assembly 378 may be assembled as shown in FIGS. 3N-3R. As shown, the manifold 334 may be provided and may include a first quadrant 380, a second quadrant 382, a third quadrant 384, and a fourth quadrant 386. A first micropump 368 may be disposed in the first quadrant 380, a second micropump 370 may be disposed in the second quadrant 382, and a third micropump 372 may be disposed in the third quadrant 384. In the illustrated embodiments, the fourth quadrant 386 includes the flow sensor interface 364. A double-sided adhesive 388 (e.g., a foam-type adhesive available from 3M, of St. Paul, Minn., USA) may be sealed against the interface surface of the manifold 334, leaving a non-adhesive covering over the lower surface 390 of the adhesive 388 until the manifold assembly 378 is ready to be mounted to the PCB 220. In this manner, for example, manifold assemblies 378 may be manufactured independently of other components of the sampling device 200 and provided for assembly. The manifold 334 may also include alignment features 392 configured to be received by corresponding alignment features (not shown) defined in the PCB 220 to facilitate proper alignment of the manifold assembly 378 on the PCB 220 in an efficient manner.

The illustrative sampling device 200 shown in FIGS. 3A-3R is not intended to suggest any limitation as to the scope of use or functionality of embodiments of the present disclosure. Neither should the illustrative sampling device 200 be interpreted as having any dependency nor requirement related to any single component or combination of components illustrated therein. Additionally, various components depicted in FIGS. 3A-3R may be, in embodiments, integrated with various ones of the other components depicted therein (and/or components not illustrated), all of which are considered to be within the ambit of the present disclosure. For example, while the manifold is illustrated as being a monolithic structure in the above figures, the manifold may be integrated into the housing of the sampling device.

Figure 4:
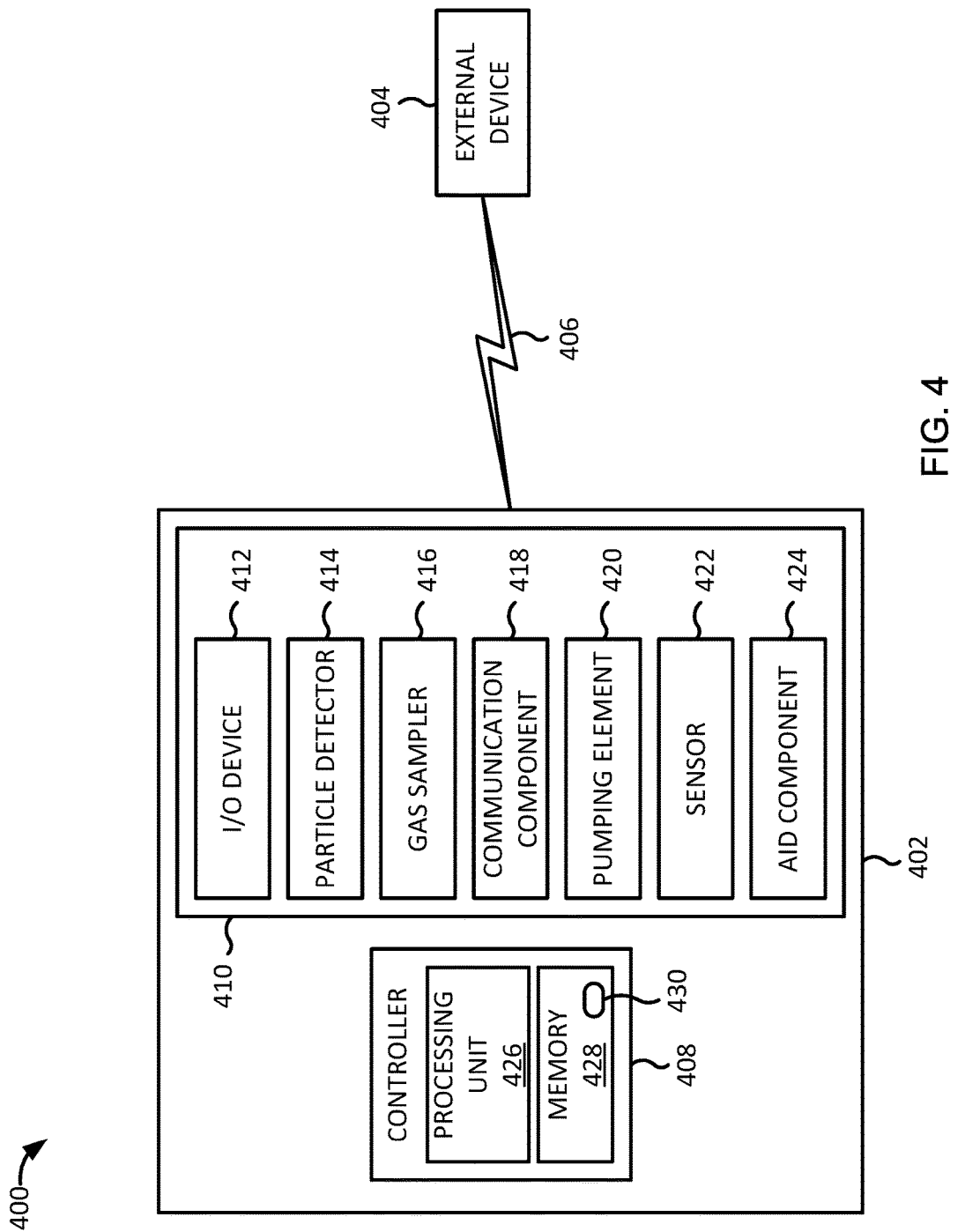
FIG. 4 is a block schematic diagram depicting an illustrative operating environment, in accordance with embodiments of the subject matter disclosed herein.

FIG. 4 is a block schematic diagram depicting an illustrative operating environment 400, in accordance with embodiments of the subject matter disclosed herein. As shown in FIG. 4, the operating environment 400 includes a portable, size-selective aerosol sampling device 402 configured to communicate with an external device 404 via a communication link 406. In embodiments, the sampling device 402 may be, be similar to, include similar features as, include, or be included in the sampling device 10 depicted in FIGS. 1A-1L, the sampling device 160 depicted in FIGS. 2A-2B, and/or sampling device 200 depicted in FIGS. 3A-3R. The external device 404 may include any one or more devices such as, for example, a smartphone, a router, a desktop computer, a server, another sampling device, an external programmer, and/or the like.

In embodiments, the communication link 406 may be, or include, a wireless communication link such as, for example, a short-range radio link, such as Bluetooth, IEEE 802.11, a proprietary wireless protocol, near-field communication (NFC), and/or the like. In embodiments, for example, the communication link 406 may utilize Bluetooth Low Energy radio (Bluetooth 4.1), or a similar protocol. The term "communication link" may refer to an ability to communicate some type of information in at least one direction between at least two devices, and should not be understood to be limited to a direct, persistent, or otherwise limited communication channel. That is, according to embodiments, the communication link 406 may be a persistent communication link, an intermittent communication link, an ad-hoc communication link, and/or the like. The communication link 406 may refer to direct communications between the sampling device and an external device 404, and/or indirect communications that travel between the sampling device and the external device 404 via at least one other device (e.g., a repeater, router, hub, and/or the like). The communication link 406 may facilitate uni-directional and/or bi-directional communication between the sampling device and the external device 404.

In embodiments, the communication link 406 may be, or include, any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The communication link 406 may include a combination of multiple networks. A variety of communication methods and protocols may be used to facilitate communication between devices 402 and 404. For example, wired and/or wireless communications methods may be used. For any given communication method, a multitude of standard and/or proprietary communication protocols may be used. For example and without limitation, protocols such as radio frequency pulse coding, spread spectrum, direct sequence, time-hopping, frequency hopping, SMTP, FTP, and TCP/IP may be used. Other proprietary methods and protocols may also be used. Further, a combination of two or more of the communication methods and protocols may also be used.

The various communications between the components of the operating environment may include any number of different types of security techniques. For example, encryption and/or tunneling techniques may be used to protect data transmissions. Additionally, or alternatively, a priority data exchange format and/or interface that are kept confidential may also be used. Authentication may be implemented using, for example, digital signatures based on a known key structure (e.g., PGP or RSA). Other physical security and authentication measures may also be used, such as security passwords and/or biometric security apparatuses (e.g., retina scans, iris scans, fingerprint scans, veinprint scans, voice, facial geometry recognition, etc.). Encryption, authentication and verification techniques may also be used to detect and/or correct data transmission errors. In embodiments, varying levels of security may be applied to communications depending on the type of information being transmitted. Additionally, in embodiments, communications among the various components of the operating environment may be enhanced using compression techniques to allow larger amounts of data to be transmitted efficiently.

As shown in FIG. 4, the sampling device 402 includes a controller 408 configured to communicate with and/or control functional components 410 of the sampling device 410. As shown, the functional components 410 include an input/output (I/O) device 412, a particle detector 414, a gas sampler 416, a communication component 418, a pumping element 420, a sensor 422, and an automatic-identification (AID) component 424. According to embodiments, the functional components may include any one or more of the components depicted in FIG. 4, and may, in embodiments include any number of components not depicted in FIG. 4. The controller 408 includes a processing unit 426 configured to communicate with memory 428 to execute computer-executable instructions 430 stored in the memory 428. In embodiments, the controller 408 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller 408 is referred to herein in the singular, the controller 408 may be implemented in multiple instances, distributed across multiple computing devices, instantiated within multiple virtual machines, and/or the like.

The I/O device 412 may refer to one or more I/O devices 412 and may include any number of different types of I/O devices such as, for example, light indicators, speakers, buttons, and/or the like. The I/O device 412 may be configured to present information to a user and/or receive input from a user. According to embodiments, the I/O device 412 may be configured to indicate a device status (e.g., on/off, active, error, etc.), receive a command from a user, and/or the like. In embodiments, the I/O device 412 may include a touch-screen interface, an LED, and/or the like.

The particle detector 414 may be a device and/or system configured to perform real-time particle detection, counting, and/or analysis. In embodiments, for example, the particle detector 414 may include an optical sensor assembly. In embodiments, for example, the controller 408 may communicate with the particle detector 414 to coordinate measurements, control the particle detector 414, and/or the like. For example, the controller 408 may facilitate altering one or more operational parameters of the particle detector 414, the pumping element 420, and/or the like, based on fluid flow velocity, and/or any other information. In embodiments, the particle detector 414 may include a filter and/or any number of different types of spectroscopy systems such as, for example, laser systems. In embodiments, the particle detector 414 may include a microscope, camera, and/or other viewing/imaging devices.

The gas sampler 416 may include a gas-sampling tube removably coupled to an airflow assembly of the sampling device 402 and configured to determine the presence, volume, concentration, and/or other characteristics of a gas. In embodiments, the gas sampler 416 may be integrated with one or more structures of the sampling device 402, removably coupled to the outside of the sampling device 402, and/or the like.

The communication component 418 may include hardware, software, and/or firmware configured to facilitate communications between the sampling device 402 and an external device 404. In embodiments, the communication component 418 may include one or more antennae, one or more receivers, one or more transmitters, one or more transceivers, and/or the like. The communication component 418 may be configured to facilitate communication using any one or more communication techniques described above with respect to the communication link 406.

The pumping element 420 may include any number of different types of pumping elements configured to provide an airflow. In embodiments, one of more of the pumping elements 420 include an ultrasonic micropump. Ultrasonic micropumps may include, for example, piezoelectric microblowers manufactured by Murata Manufacturing Co., Ltd. of Japan. In embodiments, the controller 408 may be configured to control the pumping element 420 to vary the airflow velocity. In embodiments, the controller 408 may be configured to vary the airflow in response to user input, computer-readable instructions, an output of a feedback control loop, and/or the like.

The sensor 422 may refer to one or more sensors operatively coupled to the controller 408. The sensors may be configured to directly or indirectly measure airflow velocity, mass flow rate, and/or any number of other parameters, and may include any number of different types of sensors capable of facilitating such measurements. In embodiments, the controller 408 may be configured to determine a composition of the fluid entering the device, a temperature of the fluid, force of gravity, wind speed, density, pressure, and/or any number of other characteristics of the fluid, ambient environment, and/or the like. These characteristics may be used by the controller 408 to determine the appropriate fluid flow velocity to direct the pumping element 420 to provide a certain fluid flow velocity, and may be determined based on user input, input from the sensor 422, input from additional sensors (not shown), and/or the like. In embodiments, the sensor 422 may include a global positioning system (GPS) module, an accelerometer, an inertial measuring unit (IMU), and/or the like.

The automatic identification (AID) component 424 includes a component configured to communicate, using an AID technique, with a corresponding AID component associated with a sampling assembly (e.g., the sampling assembly 22 depicted in FIGS. 1A-1H, and/or the sampling assembly 212 depicted in FIGS. 3A-3I). In embodiments, the AID technique may include at least one of an electronic-contact identification technique, a near-field communication (NFC) technique, a radio-frequency identification (RFID) technique, and/or the like. For example, in embodiments, the sampling assembly may include an RFID tag that can be read by an RFID sensor 424 disposed in the sampling device housing. Communications between the sampling assembly and the sampling device can be used to transfer information related to sampling device configuration (e.g., cyclone configuration, sampling filter characteristics, etc.) users, samples, sample processes, instructions for sampling, ambient condition measurements, and/or the like.

According to embodiments, the sampling device 402 may be, or include, monitors such as, for example, a direct reading instrument (DRI), a gas detector, a biosensor, and/or the like. In embodiments, a monitor (or component thereof) may be used to trigger (e.g., via communication with the controller 408) or control the sampling device 402. For example, in embodiments, a DRI may trigger the sampling device 402 to begin collecting particles onto an appropriate sampling filter in response to sensing a spike in a certain particle concentration level. As another example, in embodiments, a gas detector may trigger the sampling device 402 to begin sampling in response to sensing a specific gas concentration level. As another example, in embodiments, a biosensor may trigger the sampling device 402 to begin sampling in response to detecting a specific biogen concentration level.

Data and/or control signals may be transmitted between the sampling device 402 and the external device 404 to coordinate the functions of the sampling device and the external device 404. In embodiments, for example, the sampling device 402 may be configured to be programmed by the external device 404, receive sampling parameters from the external device, and/or the like. That is, for example, in embodiments, the external device 404 may be a user's mobile device that includes an application for controlling and/or programming the sampling device 402. The application may be configured to provide a user interface that enables a user to input various sampling parameters, activate the sampling device 402, retrieve operational and/or environmental parameter information from the sampling device 402, and/or the like.

According to embodiments, the external device 404 may include another sampling device such as, for example, another portable size-selective aerosol sampling device, a gas sampler, a biosensor, and/or the like, and may be configured to communicate with the sampling device 402. In embodiments, for example, one of more of the sampling device 402 and the external device 404 (or external devices 404) may be configured to be activated in response to receiving an activation signal from one of the other devices. That is, for example, the sampling device 402 may be configured to transmit an activation signal to one or more additional sampling devices 404 upon detecting a specified condition (e.g., a certain concentration of particles in the fluid, a certain type of particles in the fluid, activation of the sampling device 402, change in location of the sampling device 402, etc.). In this manner, networks of interactive and/or inter-operable sampling devices may be implemented.

The illustrative operating environment 400 depicted in FIG. 4 is not intended to suggest any limitation as to the scope of use or functionality of embodiments of the present disclosure. Neither should the illustrative operating environment 400 be interpreted as having any dependency nor requirement related to any single component or combination of components illustrated therein. Additionally, various components depicted in FIG. 4 may be, in embodiments, integrated with various ones of the other components depicted therein (and/or components not illustrated), all of which are considered to be within the ambit of the present disclosure.

According to various embodiments of the disclosed subject matter, any number of the components depicted in FIG. 4 (e.g., the sampling device 402, aspects of the communication link 406, and/or the external device 404) may be implemented on one or more computing devices. A computing device may include any type of computing device suitable for implementing aspects of embodiments of the disclosed subject matter. Examples of computing devices include specialized computing devices or general-purpose computing devices such "workstations," "servers," "laptops," "desktops," "tablet computers," "hand-held devices," "portable sampling devices," and the like, all of which are contemplated within the scope of FIG. 4, with reference to various components of the operating environment 400.

In embodiments, a computing device includes a bus that, directly and/or indirectly, couples the following devices: a processing unit (e.g., the processing unit 426 depicted in FIG. 4), a memory (e.g., the memory 428 depicted in FIG. 4), an input/output (I/O) port, an I/O component (e.g., the I/O device 412 depicted in FIG. 4), and a power supply. Any number of additional components, different components, and/or combinations of components may also be included in the computing device. The I/O component may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touchscreen device, an interactive display device, a mouse, and/or the like.

The bus represents what may be one or more busses (such as, for example, an address bus, data bus, or combination thereof). Similarly, in embodiments, the computing device may include a number of processing units, a number of memory components, a number of I/O ports, a number of I/O components, and/or a number of power supplies. Additionally any number of these components, or combinations thereof, may be distributed and/or duplicated across a number of computing devices.

In embodiments, the memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The following is claimed:

1. A portable, size-selective aerosol sampling device, comprising:
    a housing at least partially enclosing an inner chamber, the housing comprising an upper housing portion and a lower housing portion, the upper housing portion comprising a size-selective cyclone inlet;
    an airflow assembly disposed within the inner chamber and comprising a portion of an airflow path from the size-selective inlet through the housing to an airflow outlet of the housing, the airflow assembly comprising:

a portion of a printed circuit board (PCB); and a manifold configured to be sealably coupled to the portion of the PCB to define at least one airflow channel disposed between an inner surface of the manifold and an outer surface of the PCB; and a sampling filter disposed in the airflow path and configured to collect particulate matter thereon during a sampling operation of the device.

2. The sampling device of claim 1, wherein the manifold comprises a plurality of inside surfaces of the upper housing portion or the lower housing portion.

3. The sampling device of claim 1, wherein a seal between the manifold and the PCB is achieved using at least one of an adhesive and a compressible gasket.

4. The sampling device of claim 1, further comprising one or more pumping elements, each having an inlet exposed to a first environment and an outlet exposed to a second environment, wherein each outlet is sealed from the first environment at an interface with at least one of the inner surface of the manifold and the outer surface of the PCB.

5. The sampling device of claim 4, the one or more pumping elements comprising one or more ultrasonic micropumps.

6. The sampling device of claim 1, wherein the at least one airflow channel comprises a primary airflow channel, the manifold comprising:

an interface surface configured to mate with an interface portion of the outer surface of the PCB; and at least one inner channel surface defining the primary airflow channel.

7. The sampling device of claim 6, the manifold further comprising at least one additional inner surface configured to partially define at least one secondary airflow channel, wherein the at least one secondary airflow channel is configured to provide airflow to an inlet of a mass flow sensor, the mass flow sensor comprising an outlet that opens into an ambient environment having an ambient air pressure, and wherein the mass flow sensor is configured to obtain measurements to facilitate estimation of at least one of a pressure drop across a sampling filter and an aerosol mass accumulation rate onto a sampling filter, the ambient environment comprising at least one of the inner chamber and an environment outside of the housing.

8. The sampling device of claim 1, wherein the size-selective inlet further comprises at least one of a filter, and an inhalable inlet.

9. The sampling device of claim 1, further comprising an optical sensor for determining one or more air quality parameters.

10. The sampling device of claim 1, wherein the airflow path does not include tubing.

11. The sampling device of claim 1, further comprising one or more sensors mounted to the outer surface of the PCB and disposed between the inner surface of the manifold and the outer surface of the PCB.

12. A portable size-selective aerosol sampling device, comprising:

a housing at least partially enclosing an inner chamber, the housing comprising an upper housing portion and a lower housing portion, the upper housing portion comprising a sampling assembly receiver; and a sampling assembly having a coupling interface configured to be removably mated with a corresponding coupling interface of the sampling assembly receiver, the sampling assembly comprising a cyclone assembly, the cyclone assembly comprising:

a cyclone body having an at least partially conical cavity defined therein, wherein the cavity extends from a lower end of the cyclone body toward an upper end of the cyclone body;

a cyclone inlet aperture defined through the cyclone body;

a cyclone floor disposed adjacent the lower end of the cyclone body; and a size-selective cyclone outlet aperture defined through the cyclone floor.

13. The sampling device of claim 12, the sampling assembly further comprising a filter cartridge comprising a filter cartridge housing configured to house a sampling filter, the filter cartridge housing comprising:

a filter cartridge base configured to receive the sampling filter; and a filter cartridge cap detachably coupled to the filter cartridge base, wherein an upper surface of the filter cartridge cap comprises the cyclone floor.

14. The sampling device of claim 13, wherein characteristics of the size-selective cyclone are configured to allow particulate matter having a selection size to pass through the size-selective cyclone outlet aperture for deposition on a sampling filter, wherein the selection size comprises at least one of an aerodynamic diameter of between approximately 1.0 microns and approximately 10.0 microns, Respirable PM, Thoracic PM, and Inhalable PM.

15. The sampling device of claim 12, further comprising:

a first automatic-identification (AID) component associated with the sampling assembly; and a second AID component associated with the housing, wherein the first and second AID components are configured to communicate using an AID technique, the AID technique comprising at least one of an electronic-contact identification technique, a near-field communication (NFC) technique, and a radio-frequency identification (RFID) technique.

16. The sampling device of claim 12, the sampling assembly further comprising a sampling assembly skirt disposed around at least a portion of an outside surface of the cyclone body, the sampling assembly skirt comprising:

an upper wall having an upper surface that is at least approximately perpendicular to a central vertical axis of the cyclone body; and a side wall extending downward from a lower surface of the upper wall, wherein an outside surface of the side wall is configured to mate with an inner surface of the sampling assembly receiver, wherein the upper surface of the upper wall and an inner surface of the side wall at least partially define a screening chamber into which air is configured to flow before entering the cyclone, and wherein the upper wall includes at least one inlet aperture extending between the upper surface of the upper wall and the lower surface of the upper wall, configured to provide an airflow pathway between an external environment and the screening chamber.

17. The sampling device of claim 16, further comprising one or more water-release apertures defined through the sampling assembly receiver and configured to facilitate drainage of water from the screening chamber.

18. The sampling device of claim 12, further comprising an airflow assembly disposed within the inner chamber and comprising a portion of an airflow path from the cyclone inlet aperture through the sampling device to an airflow outlet of the sampling device, wherein the airflow path does not include tubing.

* * * * *